United States Patent [19]

Chaco

[11] Patent Number: 5,465,082
[45] Date of Patent: * Nov. 7, 1995

[54] APPARATUS FOR AUTOMATING ROUTINE COMMUNICATION IN A FACILITY

[75] Inventor: John Chaco, Seymour, Conn.

[73] Assignee: Executone Information Systems, Inc., Milford, Conn.

[*] Notice: The portion of the term of this patent subsequent to Mar. 1, 2011 has been disclaimed.

[21] Appl. No.: 924,101

[22] Filed: Aug. 3, 1992

Related U.S. Application Data

[63] Continuation-in-part of Ser. No. 559,196, Jul. 27, 1990, Pat. No. 5,291,399.

[51] Int. Cl.$^6$ ............... G08B 5/00; G08B 13/14; G08B 23/00; G06K 5/00
[52] U.S. Cl. ............... 340/825.54; 340/825.36; 340/572; 340/573; 340/990; 235/382
[58] Field of Search ......... 364/413.01, 413.02, 364/413.03; 235/375, 380, 376, 377, 382, 378; 340/989, 990, 992, 993, 995, 568, 572, 573, 825.54, 825.36

[56] References Cited

U.S. PATENT DOCUMENTS

| | | |
|---|---|---|
| 3,439,320 | 4/1969 | Ward . |
| 3,478,344 | 11/1969 | Schwitzgebel et al. . |
| 3,696,384 | 10/1972 | Lester . |
| 3,714,573 | 1/1973 | Gressman ............... 342/387 |
| 3,739,329 | 6/1973 | Lester . |
| 3,925,762 | 12/1975 | Heitlinger et al. ............... 340/870.09 |
| 4,023,013 | 5/1977 | Kihker ............... 235/379 |
| 4,052,567 | 10/1977 | MacKay . |
| 4,207,468 | 6/1980 | Wilson ............... 250/341 |
| 4,225,953 | 9/1980 | Simon et al. . |
| 4,275,385 | 6/1981 | White ............... 340/825.49 |
| 4,536,646 | 8/1985 | Adams et al. ............... 235/377 |
| 4,553,267 | 11/1985 | Crimmins . |
| 4,649,385 | 3/1987 | Aires et al. . |
| 4,672,182 | 6/1987 | Hirokawa ............... 235/436 |
| 4,677,657 | 6/1987 | Nagata et al. ............... 379/63 |
| 4,725,694 | 2/1988 | Auer et al. ............... 178/18 |
| 4,757,553 | 7/1988 | Crimmins . |
| 4,835,372 | 5/1989 | Gombrich et al. ............... 235/375 |
| 4,864,115 | 9/1989 | Imran et al. ............... 235/492 |
| 4,882,473 | 11/1989 | Bergeron et al. ............... 235/380 |
| 4,906,853 | 3/1990 | Linwood et al. ............... 250/551 |
| 4,916,441 | 4/1990 | Gombrich ............... 345/169 |
| 4,955,000 | 9/1990 | Nastrom . |
| 4,977,619 | 12/1990 | Crimmins . |
| 4,984,994 | 1/1991 | Yamamoto ............... 439/267 |
| 5,017,794 | 5/1991 | Linwood et al. . |
| 5,027,314 | 6/1991 | Linwood et al. . |
| 5,038,800 | 8/1991 | Oba ............... 128/696 |
| 5,077,666 | 12/1991 | Brimm et al. ............... 364/413.02 |
| 5,119,104 | 6/1992 | Heller . |
| 5,157,737 | 10/1992 | Sklarew ............... 382/13 |
| 5,164,985 | 11/1992 | Nysen et al. ............... 380/9 |
| 5,173,883 | 12/1992 | Ilie et al. ............... 368/90 |
| 5,231,273 | 7/1995 | Caswell et al. ............... 235/385 |
| 5,237,609 | 8/1993 | Kimura ............... 380/3 |

FOREIGN PATENT DOCUMENTS

| | | |
|---|---|---|
| 2190525 | 11/1987 | United Kingdom . |
| 2193359 | 2/1988 | United Kingdom . |

Primary Examiner—David M. Huntley
Assistant Examiner—Stephen R. Tkacs
Attorney, Agent, or Firm—Dilworth & Barrese

[57] ABSTRACT

A distributed data processing network includes multiple memory card databases at terminal nodes of the network. The network is programmed to automatically perform routine communications operations such as conveying identification information between the terminal nodes and interior nodes. The network is implemented in a hospital environment and the databases include information on patients and hospital personnel. Using the automatic communications facilities of the network patient information from the database is displayed at a nurse station when the patient initiates a nurse-call or automatically when medication, also recorded on the card, is due. In addition, the system may be used to locate hospital personnel and equipment, to audit the use of controlled substances and to automatically assemble emergency response teams.

30 Claims, 25 Drawing Sheets

PATIENT STATION MAIN LOOP

CALL NURSE STATION

STORE DATA IN DESIGNATED MEMORY AREA

Fig. 10 PROCESS INTERNAL TIMER

Fig. 8 STORE EXTERNAL DATA

PROCESS LIGHT PEN DATA

BADGE TRANSMITTER PROCESS

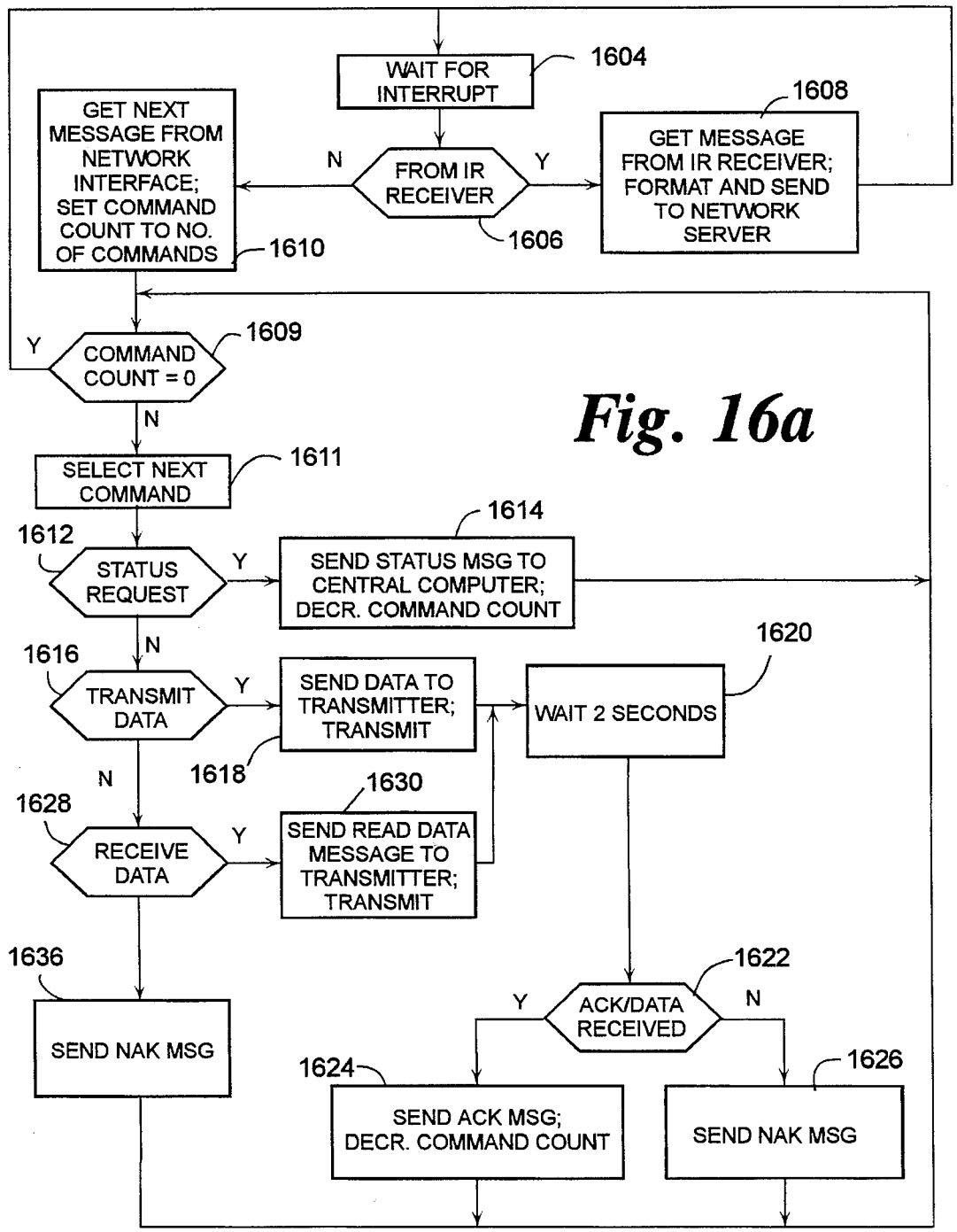
STATIONARY TRANSCEIVER PROCESS

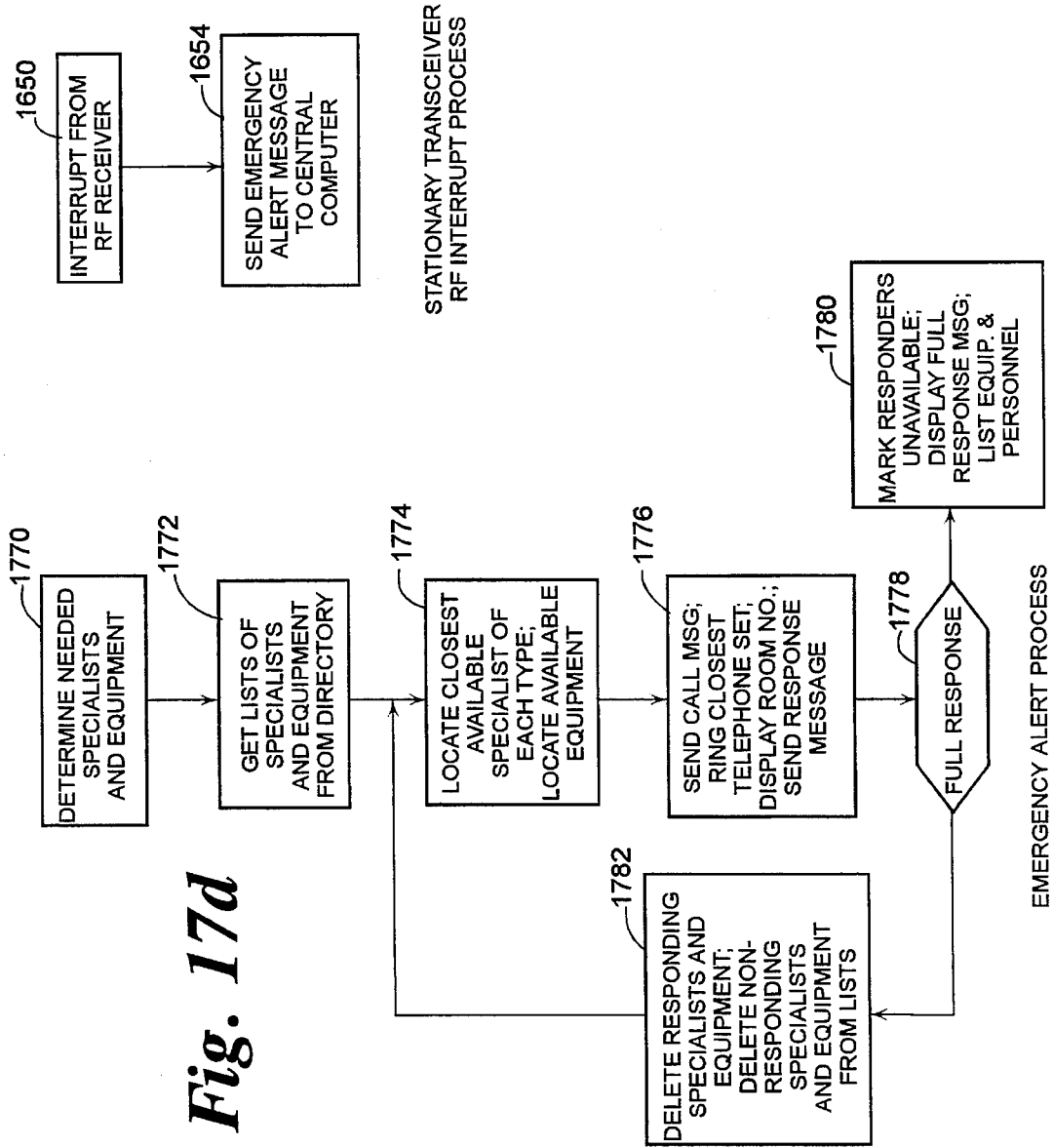

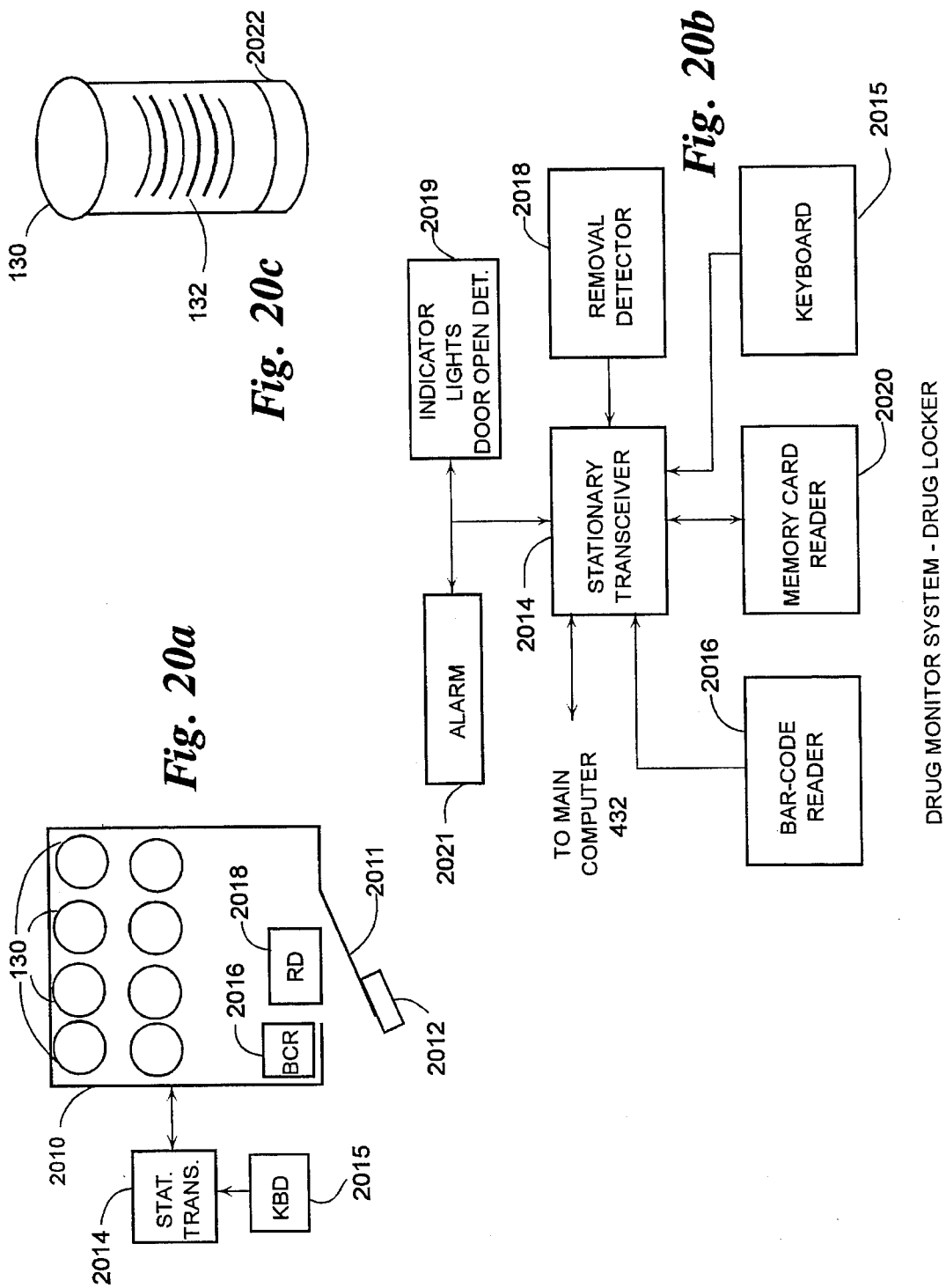

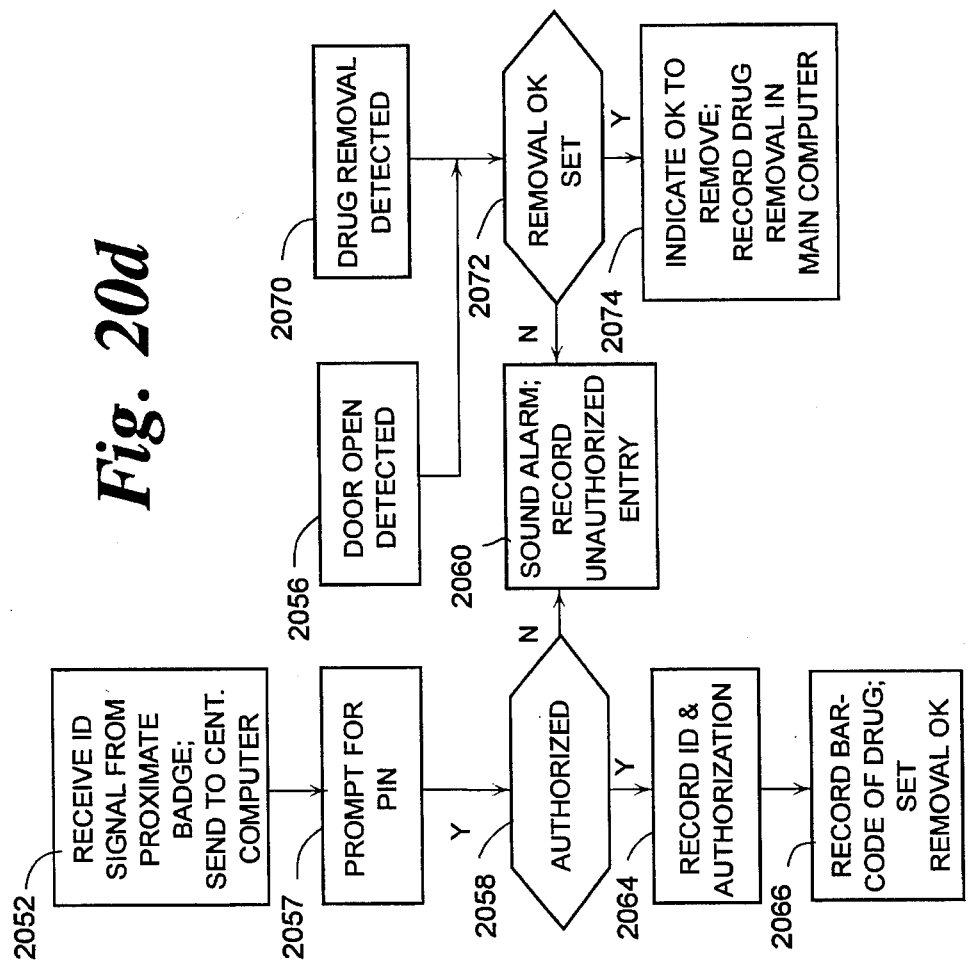

APPARATUS FOR AUTOMATING ROUTINE COMMUNICATION IN A FACILITY

This application is a Continuation In Part of U.S. patent application Ser. No. 07/559,196 now U.S. Pat. No. 5,291,399 which was filed on Jul. 27, 1990.

FIELD OF THE INVENTION

The present invention is directed to a portable personal database and to an apparatus for accessing and enabling the database which may be used by patients and caregivers in a hospital environment and in other analogous environments. In particular, the invention concerns such a database implemented in a data storage medium having the portability of a credit card, which when coupled with an identification badge and enabled, acts to communicate data with other data processing apparatus via a ubiquitous network.

BACKGROUND OF THE INVENTION

As medical technology has developed to provide treatments for a greater number of medical conditions, and as hospitals have become automated to cope with chronic personnel shortages, the volume of information that is maintained for each patient has grown rapidly. As a result of this increase in information, it is often difficult for caregivers such as physicians and nurses to quickly find critical data about a patient.

To more fully understand the problem, consider the types of data which may be maintained for an individual patient. The hospital may want to know the name, address and insurance carrier for the patient as well as any special dietary, environmental or physical space requirements. The attending physician may want to know the patient's condition, medical history and recent vital sign data. If the patient has had any diagnostic tests such as X-rays or ultrasound images made at this hospital, or at any other hospital, the attending physician may want to compare these test results with the results of newer tests to see how the patient's condition has progressed. In addition, if any medication has been prescribed, the physician may want to know the identity of the medication, when the last dose was taken and how the patient has complied with the dosage schedule.

The nursing staff covering the patient's room may want to have some indication of the patient's condition at the nurse station when the patient presses the nurse call button. For example, if the patient has been admitted for a heart condition, it would be helpful if any recent vital signs that may indicate the onset of a heart attack could be displayed at the nurse's station when patient presses the call button.

This type of information may be especially helpful when, due to a shortage of nurses or to an emergency situation, routine calls must be delayed. This information may also be helpful to a temporary nurse who is not familiar with the patients or with the hospital procedure.

Patient billing presents another data-keeping problem for hospitals. Charges for the physician, diagnostic laboratory and pharmacy may be separate from the hospital charges. In addition, many hospitals are allowing patients to charge non-essential items such as magazines and books to their hospital accounts. Currently, due to the time required to process these items through the hospital billing system and the insurance carrier, the charges that must be paid by the patient may not be known until several months after the hospital stay. Furthermore, some insurance carriers, such as Medicare, pay the physician based on the actual time spent with the patient. Using the present data gathering methods, billing data of this type may be difficult to obtain and to verify.

Recently, memory cards and smart cards have been used to hold a patients billing information and medical records. Three different types of cards, each about the size and thickness of an ordinary credit card, have been used for these purposes. One type of card has a non-volatile memory such as a magnetic stripe or a medium on which information may be recorded using a laser. These cards may hold a relatively large amount of information but this information can only be read by a relatively large and complex card reader. Another type of card includes a non-volatile memory such as an electrically alterable read only memory (EAROM) with external contacts on the surface of the card. Data stored in a memory of this type may be read using circuitry that is relatively inexpensive and compact. The third type of card combines a microprocessor with the non-volatile memory. In this configuration, the card may include programming to implement a security system which is designed to prevent unauthorized access to data on the card.

An exemplary system in which hospital billing information is kept on a memory card is described in an paper by A. Matsunobu et al. entitled "Kapiolanai Women's And Children's Medical Center" Computing Healthcare Vol 7, No. 6 PP 20–26, 1986. A system for keeping patient records on a laser card system is described in a paper by J. H. U. Brown et al. entitled "A New Patient Record System Using The Laser Card" Optical Information Systems, Vol 8, No. 4, PP 156–161 July–August 1988. Two systems which use a memory card to hold patient records are described in a paper by R. C. Livermore entitled, "Health Service Applications In England And Wales" Smart Card 88, PP 5–10, June 1988.

All of these systems merely record the information on the card so that it may be read by a caregiver at a later time. These systems fill a need by allowing the caregiver to obtain the medical records directly from the patient rather than having to request the data from the various hospitals, physicians and pharmacists which have served the patient. None of these systems provides for any automatic interaction with information stored on the card.

Another problem faced by caregivers and by hospital administrators is determining the location of key personnel and equipment. In an emergency it may be of critical importance to be able to quickly locate the attending physician and to communicate the nature of the emergency situation. Moreover, when special equipment is required to treat an emergency condition, it is desirable that this equipment be quickly located with a determination as to its availability. These needs should be considered with security concerns in mind, so that certain items do not become easily accessible to unauthorized personnel.

Current systems for locating personnel within a hospital rely on audio paging systems, sign-in and sign-out sheets and broadcast paging systems. In a given situation, the audio paging system would be tried first. This system may not be effective if the person to be located is in an area where the paging system is not functioning properly or has been turned down, or if the person has left the hospital. After an unsuccessful audio page, the sign-in and sign-out sheets may be checked. If, however, the person to be located forgot to use the sign-out sheet, critical time may be lost in a second attempt to use the audio paging system. In addition, a search of the sign-in and sign-out sheets may require more time than is available in an emergency situation.

When the person to be located is outside of the hospital, broadcast paging systems are often the best way to convey an important message. These systems require the individual trying to locate the person to call a paging service, leave a message, wait for the paging service to send the message to the individual's pocket pager and then wait for the person being paged to call the paging service, receive the message and respond. This system is too time consuming and unwieldy for use inside the hospital environment.

Physicians who have a private practice and who are associated with a hospital may have difficulty receiving emergency calls while they are in the hospital but not in their hospital office. Calls of this type may be handled either through the audio paging system of the hospital or through a broadcast paging system. Neither of these solutions is particularly desirable, since, the physician may not hear or understand the message sent through the audio paging system and may not wish to be interrupted by a pocket beeper while attending to a patient in the hospital.

Another problem with audio paging systems used in a hospital environment is noise pollution. These systems are often louder than necessary and may add an element of stress to an environment where stress is desirably kept to a minimum.

In addition to locating caregivers, it may also be desirable to quickly locate patients who are not in their rooms. This is particularly true for patients that have recently been moved, say from an intensive care unit to a room, or for patients who tend to wander or who have memory problems. Patients such as these may not realize they are being paged through an audio paging system or, if they do, may be unable to respond. In these instances, hospital personnel must be available to search for the patients or the patients must be restrained to prevent them from wandering.

Exemplary existing locator systems use either radio frequency signals or infra-red signals to communicate the position of a mobile individual or object to a network of receivers. One such system, the InfraCom™ Locating And Signaling System available from United Identification Systems Corp. is designed for use in a hospital environment. Using this system, a network of infra-red transceivers located throughout a hospital can both transmit data to and receive data using a battery-operated badge worn by hospital personnel or attached to the equipment to be located. This badge transmits a programmed identification signal to the network allowing the position of the badge to be indicated on a floor plan of the hospital.

Another exemplary system, the TELOC PLS Personnel Locator System available from TELOC INC., also uses two-way infra-red signalling to communicate the position of a battery powered badge in a distributed sensor network. In addition, the TELOC system may be coupled to a private branch exchange (PBX) to allow telephone calls for an individual to be routed to the telephone that is closest to the badge or to direct an intercom message to that telephone, thus providing an alternative to an audio paging system.

Each of these systems is limited in the data that may be conveyed between the stationary transceiver network and the transceiver on the badge. In the described systems, only identification information and an indication that switches, which are located on the badge, have been activated may be transmitted from the badge.

Furthermore, if the transceiver on the badge fails or is damaged, a blank badge must be programmed to take its place. This programming operation may be time consuming, leaving the individual or the piece of equipment invisible to the locating system for that period of time.

Yet another problem faced by hospitals is in preventing unauthorized access to restricted areas, such as drug lockers and hospital pharmacies. Currently, these areas require special security measures, such as guard personnel or complex electronic apparatus to verify the identity of an authorized individual. These security measures are an annoyance to those who are subject to them and may increase the response time to an emergency situation when a critical medication is only available in the drug locker.

Although the discussion so far has focused on the hospital environment, other institutions have similar problems. For example, in correctional institutions, it may be necessary to quickly locate guards or trustees to either respond to a disturbance or to ensure that there is sufficient surveillance of the prison grounds. In an emergency, where, for example, a guard is being attacked by an inmate, it may be desirable for the guard to be able to quickly alert a central facility so that reenforcements may be sent. To provide this type of warning, the guards at many correctional facilities rely on walkie-talkies. When the situation develops quickly, however, there may not be time for the guard both to use the walkie-talkie and to protect himself against the attacker.

Many industrial security systems augment electronic intruder detectors with hired guards who follow a fixed route through the facility. To ensure that these guards walk the designated route at the appointed times, the guards may be required to carry a clock mechanism into which keys, found at key-stations along the way, may be inserted. These keys are designed to be inserted only in a prescribed order. The clock mechanism records the time at which the keys were inserted to provide a record of when the guard passed the key station. Systems of this type are subject to abuse if, for example, short-cuts exist between successive key stations. Moreover, the clock mechanisms tend to be bulky and may impede the guard in his investigation of an abnormal situation.

A night watchman at an industrial plant may have the same need as a prison guard to signal for help in an emergency situation, and, like a prison guard may not have time to use a walkie-talkie.

Another institution in which data keeping is important but often burdensome is in colleges and universities. In this environment it may be desirable to know what courses a student is taking, whether the student resides in on-campus housing and, if so, to know the student's address. The college administrators may also want to know if a particular student has an outstanding balance on his tuition bill. In addition, the student may want to be able to charge expenses to an account which is sent directly to his parents.

In many colleges and universities, the databases which keep track of this type of information are not integrated. Some information may only be available from a terminal coupled to a central computer while other information may only be recorded in a paper filing system.

SUMMARY OF THE INVENTION

The present invention is embodied in a portable personal database which contains identifying and other information about an individual, and in an apparatus associated with the portable personal database, removably coupled to the database and configured to convey data from the database to a remote transceiver.

According to a first aspect of the invention, a base unit, which may contain several of the associated database, is configured to read the identifying and other information from the database and to impart this information to an associated apparatus. The base unit causes the database and its associated apparatus to form an entity, capable of transmitting the identifying and other information to the remote transceiver. This entity may be an identification badge for hospital personnel.

Data on the database may be transmitted to and received from fixed transceivers located, for example, in ceiling fixtures distributed around the hospital. In addition to performing routine communication, such as signing into and out of the hospital, the combination of the memory card and the transmitter can be used to locate key personnel and equipment, to ease the security requirements for accessing controlled substances and to forward calls to a telephone located in close proximity to the person being called.

According to a second aspect of the invention, the database contains a predetermined personal identification code, and the base unit is adapted to ask the user to input a personal identification code. The base unit imparts the identifying information to the associated apparatus only if the entered personal identification code matches the predetermined personal identification code. The base unit serves as a time clock, by being able to calculate, store and display the time during which the database is coupled to its associated apparatus.

According to a third aspect of the invention, the database/associated apparatus entity continually transmits an identification signal to the remote transceiver so that the location and direction of travel of the entity can be determined. The entity makes this transmission at regular time intervals. The time interval used by each entity is different and is assigned based on a random number generator to avoid the potential overlap of identification signals from various entities.

According to a fourth aspect of this invention, the remote transceiver is coupled to a central processing unit, which has a list of predetermined authorized identification signals, and the remote transceiver is installed near a secured area. The remote transceiver receives the ID signal and automatically determines the identify of an individual whenever that individual's database/associated apparatus is within a certain distance from the remote transceiver. The remote transceiver compares the signal emitted by the entity with its list of predetermined authorized identification signals. If there is a match, the remote transceiver transmits an access signal to the lock of the secured area.

A fifth aspect of the invention is similar to the fourth aspect, except the central processing unit has a list of authorized personal identification codes. In this aspect, the installed transceiver automatically prompts a personal identification code, which must be matched both to the list contained by the central processing unit and to the code stored on the database itself for access to be granted.

According to a sixth aspect of the invention, the database/associated apparatus becomes disabled if the database is removed from the associated apparatus for more than forty-five seconds or if the database is coupled to the associated apparatus for more than nine hours.

According to a seventh aspect of this invention, the apparatus also has a network which has a central processing unit for collecting and processing information. This central processing unit is electronically coupled to several of the remote transceivers.

According to an eighth aspect of this invention, a second apparatus associated with a portable database is coupled to the database and can retrieve and transmit the identifying and other information without requiring an additional unit, such as the base unit.

According to a ninth aspect of the invention, the database is a memory card associated with the second apparatus and includes medical information about the individual in addition to the identifying information. The second associated apparatus includes a patient station, configured to accept the personal database and to convey the medical information along with the identifying information to a central nurses station when a nurse call operation is initiated.

According to a tenth aspect of the invention, the second associated apparatus is a portable wireless transceiver wherein information is entered by a user, such as a nurse. The second associated apparatus then transmits this information to a remote transceiver, which in turn transmits it to the central processing unit of the network. The information could be entered to the second associated apparatus either by using a keyboard, a touch-responsive screen having icons or a voice recognition system.

According to an eleventh aspect of the invention, the database is augmented by machine-readable identifying information attached to the individual, and the apparatus includes portable means for reading the attached machine-readable identifying information, for verifying it against the identifying information in the personal database and for conveying any mismatch between the machine-readable information and the identifying information in the database to the remote transceiver.

According to a twelfth aspect of the invention, the associated apparatus includes a radio transmitter which broadcasts a radio signal to convey auxiliary information to the remote transceiver.

According to a thirteenth aspect of the invention, the database includes information relating to the amount of time that it is coupled to the second associated apparatus, from which the remote transceiver as a measure of the time spent treating an individual. A fee for services rendered is calculated based on this measurement. In this aspect, the second associated apparatus is capable of simultaneously accepting and reading two portable database, one of which is used to corroborate the time spent.

According to a fourteenth aspect of the invention, the second associated apparatus includes means for momentarily changing the method by which the information is broadcast.

According to a fifteenth aspect of the invention, the apparatus is used in a hospital with a remote transceiver in each room. Each transceiver is capable of receiving transmissions from the associated apparatuses in its particular room, and the transceivers are connected to a central processing unit to form a network.

According to a seventeenth aspect of the invention, the associated apparatus is coupled to a telephone set which is coupled to a telephone network and the remote receiver is coupled to another telephone set coupled to the telephone network and the remote receiver includes means for changing information in the database while it is coupled to the telephone network.

BRIEF DESCRIPTION OF THE DRAWINGS

FIGS. 5 through 10 are flow-chart diagrams which illustrate the operation of the patient station shown in FIG. 2.

FIGS. 16a and 16b are flow-chart diagrams which illustrate the operation of the transmitter receiver unit shown in FIG. 15.

FIGS. 17c and 17d are flow-chart diagrams which illustrate the use of the system as a personnel and equipment locator and for handling an emergency alert condition.

FIG. 20a is a cut away top plan view of a drug locker which includes an embodiment of the present invention.

FIG. 20b is a block diagram of a drug locker monitoring system suitable for use with the drug locker shown in FIG. 20a.

FIG. 20c is a perspective drawing of a medication container which may be used with the drug locker monitoring system shown in FIG. 20b.

FIGS. 20d and 20e are flow-chart diagrams which illustrate the operation of a drug auditing system using the drug locker monitoring system shown in FIG. 20b and the patient station shown in FIG. 4.

FIG. 21b is a flow-chart diagram which illustrates the operation of a student-advance electronic funds transfer system which may be implemented on the student information system shown in FIG. 21a.

DETAILED DESCRIPTION

Overview

The present invention has application wherever routine communication may be automated. Many of the features of this invention may be illustrated by a system implemented in a hospital environment. Accordingly, for the sake of brevity, the detailed description of the invention presented below is primarily shown in a hospital environment. It is contemplated, however, that the invention has a much broader range of applications.

All of the exemplary embodiments of the invention described below use a memory card as a personal database. As used herein, a memory card is a device approximately the same size and shape as an ordinary credit card which includes a non-volatile programmable memory. In the card used in the embodiments described below, two types of memory are used: an electronically erasable read only memory (EEROM) located internal to the card and a magnetic stripe located on the surface of the card. It is contemplated, however, that other forms of internal memory, such as a ferro-electric RAM or a CMOS memory with an integral battery, may be used. It is also contemplated that the functions described below may be implemented with other types of external memory, such as laser card technologies which either augment or replace the card memory.

Figure 11B:
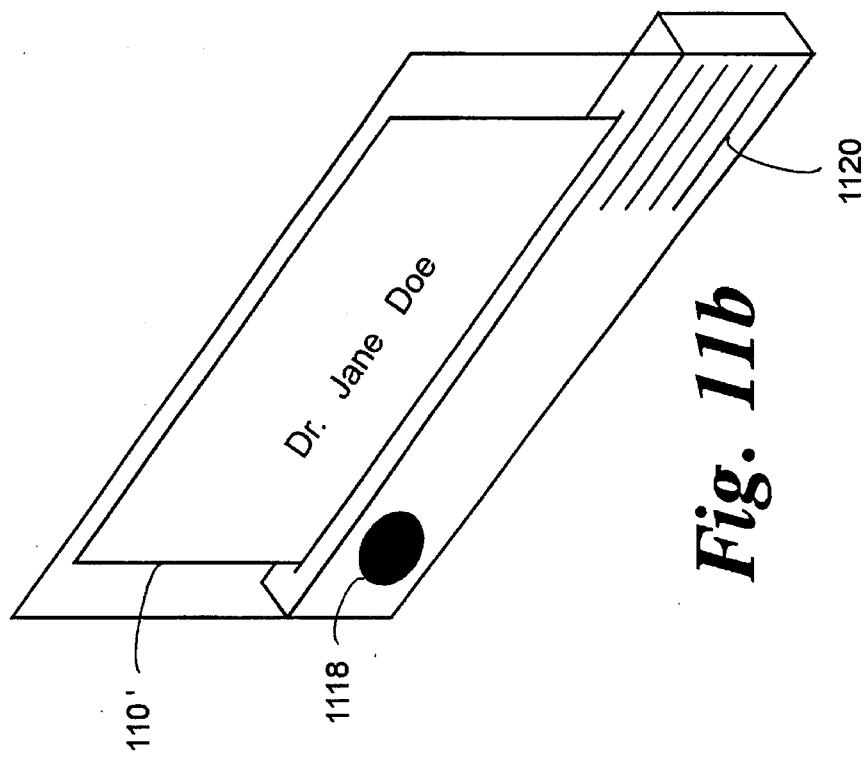
FIGS. 11a and 11b are perspective drawings of a portable transceiver unit suitable for use with the present invention.
Figure 11A:
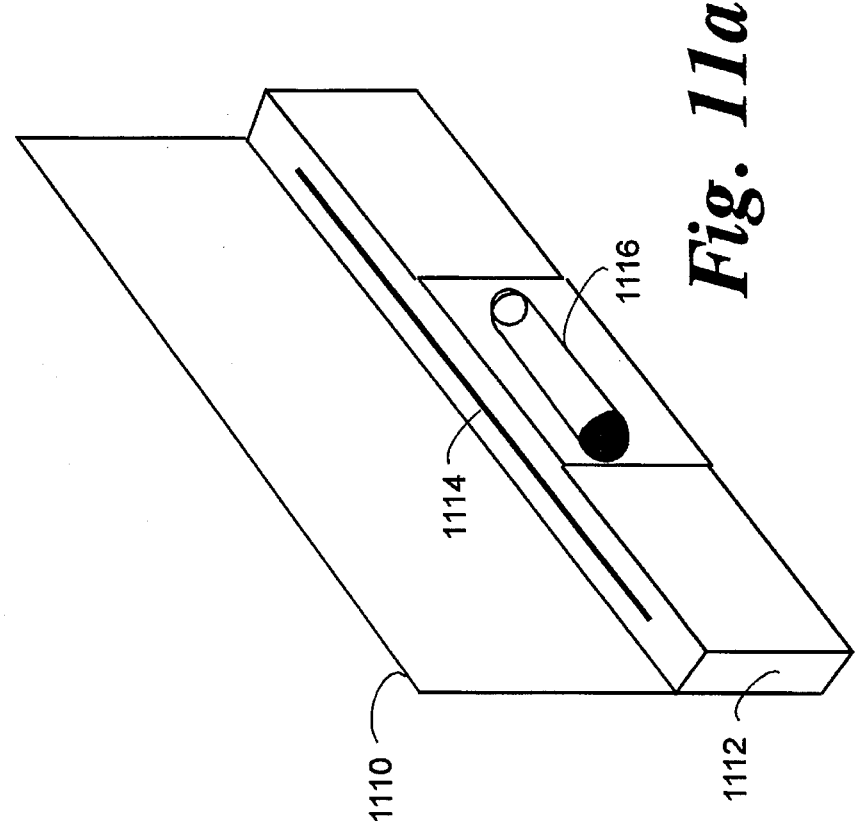
Figure 13:
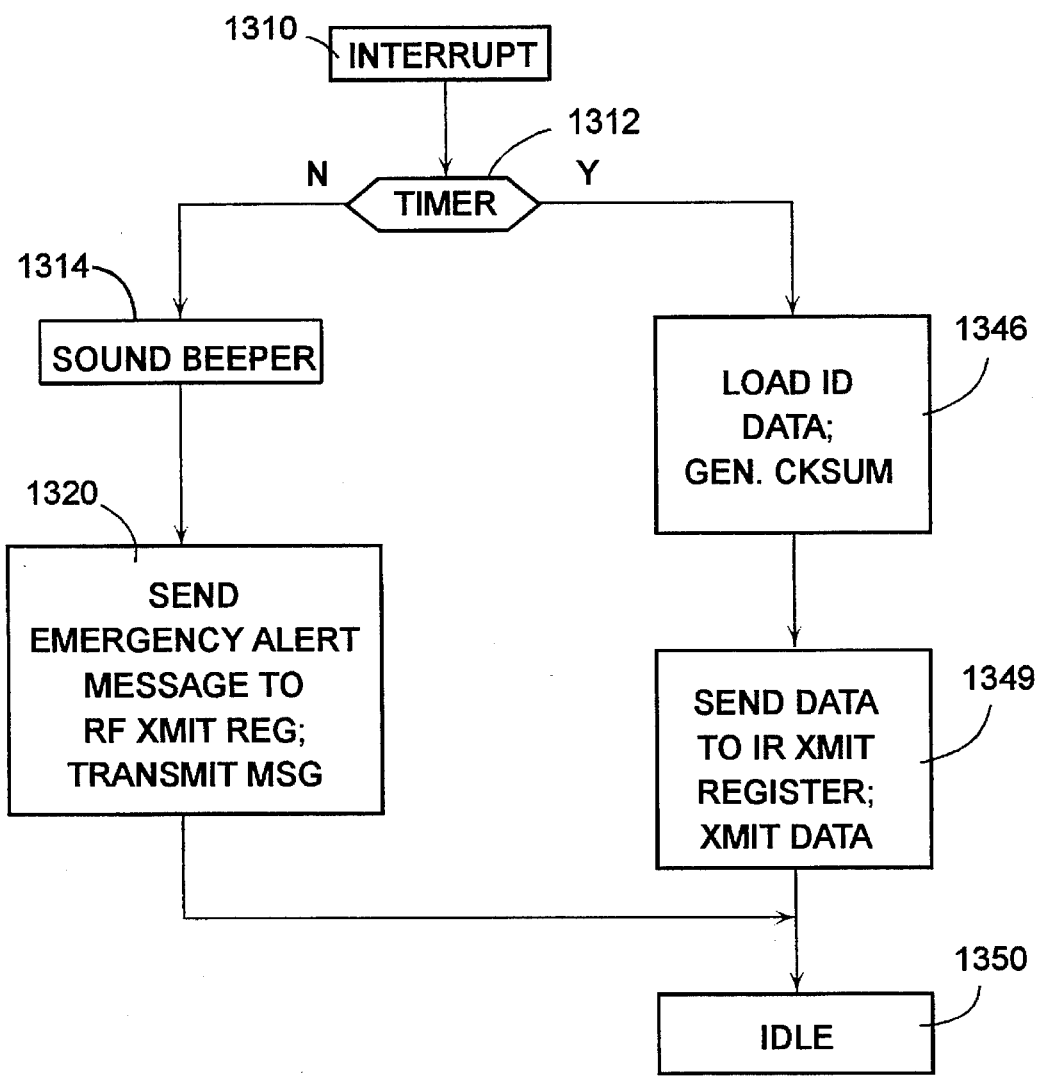
FIG. 13 is a flow-chart diagram which illustrates the operation of the portable transceiver unit shown in FIG. 12.
Figure 22:
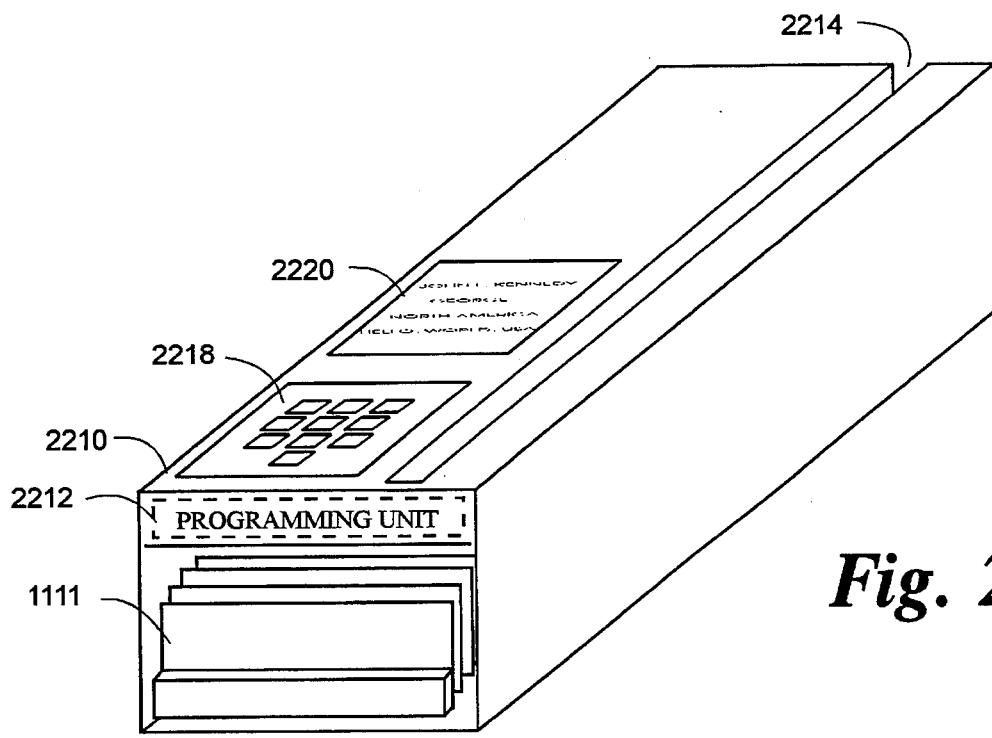
FIG. 22 is a perspective drawing of an exemplary base unit suitable for use with the portable transceiver units shown in FIGS. 11a and 11b.

A first embodiment of the invention described below uses the memory card to augment features that may be provided by a transmitter, which may appear as an identification badge. FIGS. 11a and 11b show typical transmitters which are removably coupled to the memory card. A memory card contains, for example, the name of the medical staff worker who is to wear the badge, the individual's authorization code, and other information. In this embodiment, the identification badge/transmitter is unable to transmit the information contained by the memory card unless it is effectively mated with a memory card by a base unit, as shown in FIG. 22. In FIG. 13 the sequence of how the identification badge transmitter transmits an identification signal is detailed. Using these badges, a ubiquitous network and a central computer, medical staff can quickly and easily be located.

Another embodiment described below involves the use of the memory card to again be coupled with an identification badge transmitter to continually transmit an identification signal. A fixed receiver, responsive to the identification signal, is installed near a secured area. This fixed receiver has means for receiving the ID information and automatically determining the identity of any individual within a predetermined distance and determining whether that individual is authorized, as shown in the sequence of steps of FIG. 20d. This system automatically records the identify of the person removing the drugs and the drugs that are removed. In addition, the system records when the drugs are administered and the identities of the patients to whom they are given.

In another embodiment of the invention, the identification badge transceiver becomes disabled if either (1), the badge is detached from a memory card for more than forty-five seconds, or (2) the badge is coupled to the memory card for more than 9 hours.

Another embodiment of the invention described below uses the memory card to augment the features that may be provided by a patient station in a hospital. Two types of memory cards may be used: a first type containing non-volatile memory which actually holds data on the patient and a second type which only holds identification information that may be used to locate the patient data in a remote or central database.

Figure 2:
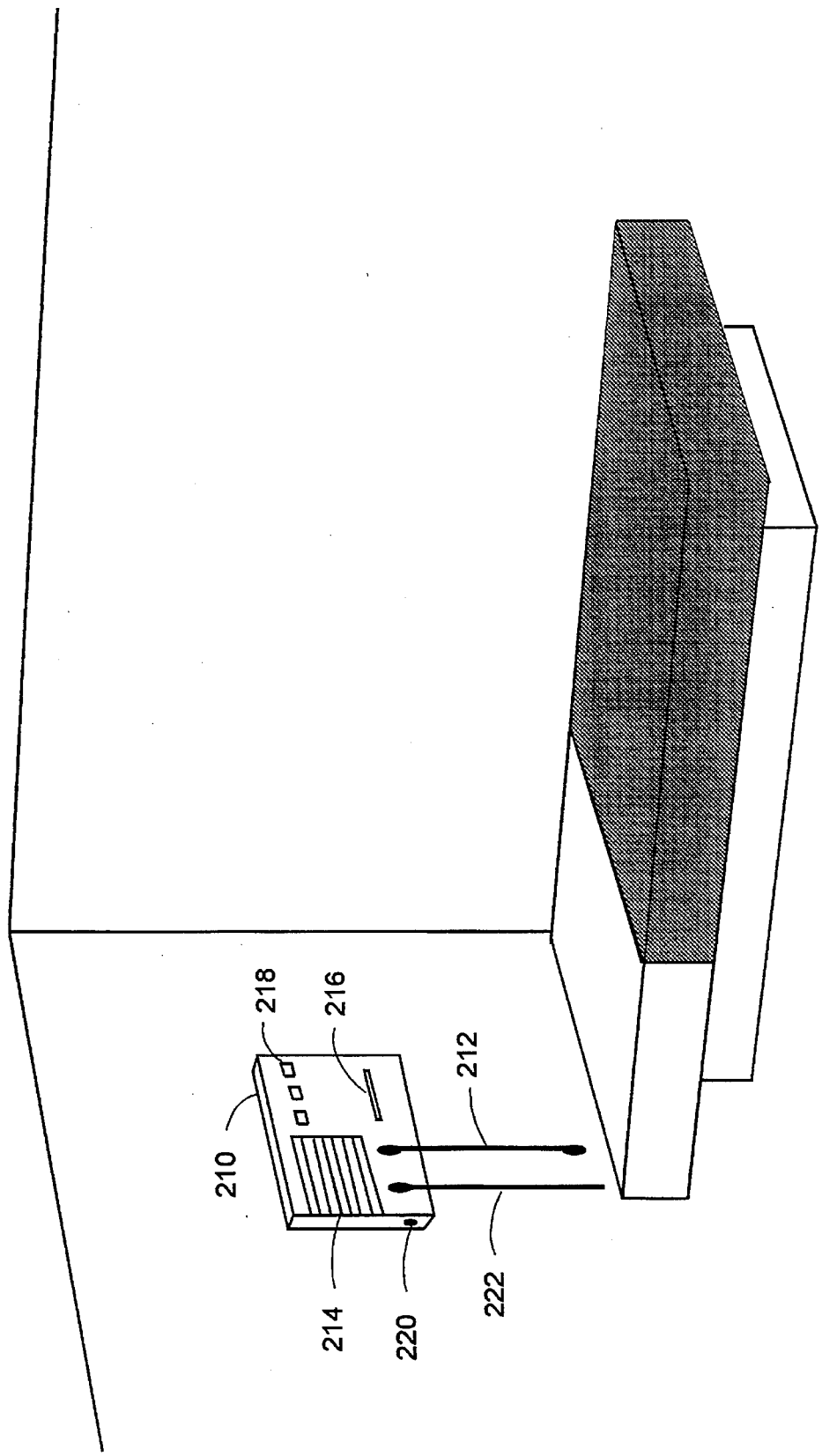
FIG. 2 is a perspective drawing of a portion of a patient room which includes a patient station suitable for use in the present invention.

In the first embodiment, the memory card includes information about the patient. FIG. 2 shows a typical hospital bed located in close proximity to a patient station 210. A memory card containing, for example, the patient's name and reason for admission as well as an abbreviated medical history is inserted in slot 216 of the patient station 210. When the patient squeezes the bulb of the nurse call device 212, the patient station 210 transmits selected information stored on the card to the central nurse station where it is displayed on a CRT monitor (not shown in FIG. 2).

The information stored in the card may include prescription information and, optionally, the most recent few minutes of vital sign data, such as may be provided by an electrocardiogram, for example. This display enables the duty nurse at the station to quickly determine the importance of a call and to respond accordingly. As described in detail below, the card may be programmed with prescribed medication for the patient. In this instance, a call to the central nurse station may be automatically generated to remind the duty nurse that it is time to administer the medication. Also, the apparatus could include portable means for reading identification, medication or other information.

Alternatively, the memory card may be the type which stores data, for example, on a magnetic stripe. Since the storage capacity of this type of card is relatively small, it may hold only identification information which is used as an index to locate information about the patient which is stored in the patient station 210 or in a database controlled by a centrally located computer. In this embodiment of the invention, the patient station would desirably include a magnetic stripe reader and the identification information may be used as an index into the locate the information in a designated memory area.

Figure 23:
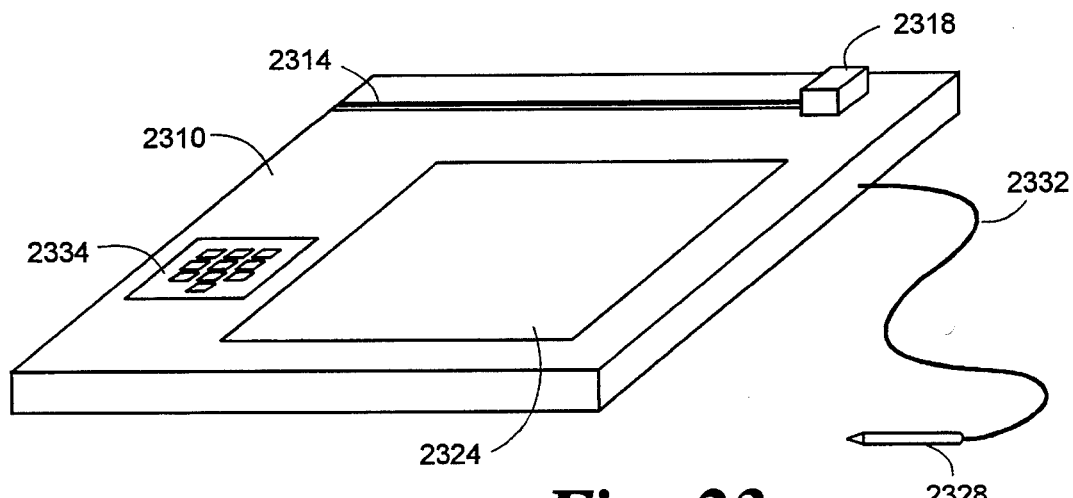
FIG. 23 is a perspective drawing of a portable nurse station suitable for use with the network shown in FIGS. 4 and 14.

Another embodiment of the invention described below uses the memory card and a portable transceiver which is capable of transmitting information entered by medical staff to the remote transceivers. This transceiver is shown in FIG. 23 with different mechanisms for entering data. This portable interface has similar data communications capability to the nurse station.

In another described embodiment, the smart card is used with a secure data communications device to automate billing operations, such as those for Medicare, where the amount the physician may bill is determined, at least in part, by the amount of time spent with the patient. This device, which would remain in the physician's office, records the amount of time that both the physician's card and the patient's card are inserted and automatically reports all patient activity to a central database at the end of the day. This embodiment of the invention, may also have a port for accepting an additional memory card, allowing a corroborating witness to be present to verify proper billing. This system is described with reference to FIG. 18.

Another embodiment of the invention described below describes the ability of the transmitter to transmit an IR signal or to momentarily transmit an RF signal used to broadcast information in an emergency. FIGS. 13 and 16d describe the sequence of steps used to implement this aspect of the invention.

A final embodiment of the invention is described with reference to FIGS. 21a and 21b. This embodiment concerns uses of a memory card in an academic environment. In one described use of the card, a student may receive an electronic funds transfer, which is recorded on the card, using a special telephone located in his dormitory room. The card may also be used to allow the student to gain read-only access to centrally stored academic data or to gain read-write access to a campus bulletin board.

DETAILED DESCRIPTION OF EXEMPLARY EMBODIMENTS OF THE INVENTION

Figure 1A:
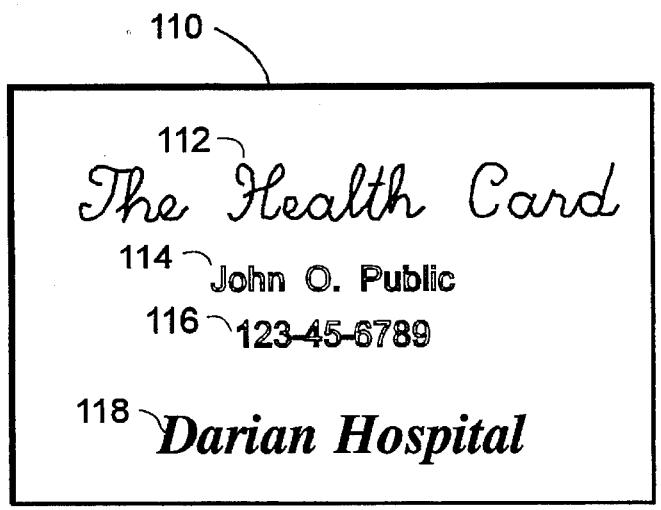
FIGS. 1a and 1b are respective front plan and back plan drawings of a personal database suitable for use in the present invention.
Figure 1B:
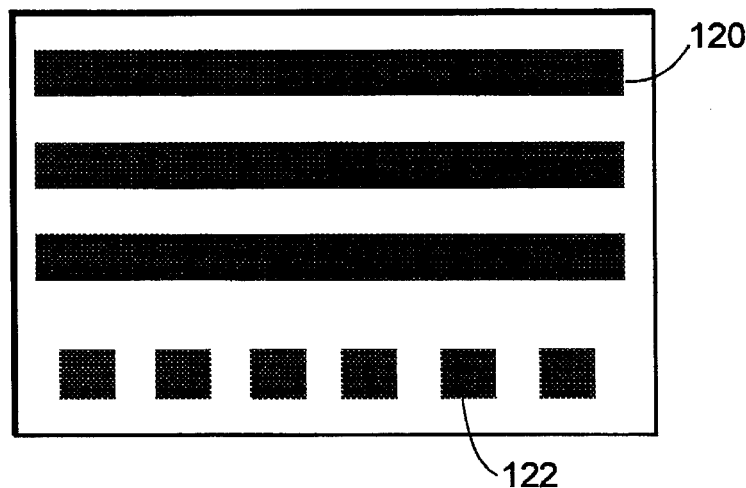

The memory card 110 used with these exemplary embodiments of the invention is illustrated in FIGS. 1a and 1b. As shown in FIG. 1a, the card 110 is approximately the same size and has the same physical characteristics as an ordinary credit card. The front of the card may include a printed logo, 112, which identifies the provider of the card, identifying information such as the person's name, 114 and ID number 116, as well as a legend, 118, identifying the hospital that issued the card.

The back of the card may include auxiliary, external data storage 120 and electrical contacts 122 for interfacing with the internal circuitry of the card. The auxiliary data storage 120 may include magnetic stripes, as shown in FIG. 1b, or a medium compatible with a laser card device. The electrical contacts 122 may be in the form of external or internal ohmic contacts, or electromagnetic contacts, such as are disclosed in U.S. Pat. No. 4,798,322 to Bernstein et al. CARD READER/WRITER STATION FOR USE WITH A PERSONAL MEMORY CARD USING DIFFERENTIAL DATA TRANSFER.

An exemplary memory card, which uses ohmic contacts and does not have any auxiliary data storage is the memory card component of the PC3™ system available from PC3 Inc. This exemplary memory card includes 16,384 (16 k) bytes of EEROM. The exact format of the data on the card is unimportant for this description of the invention since it would change with the application.

A second exemplary memory card uses only the auxiliary data storage and has no ohmic contacts or internal data storage. This card may be any of a number of commercially available cards which include a magnetic stripe.

The memory card is a portable database of information. For purposes of this description, the card has two embodiments, although others are possible. First, the card is a database containing only identifying information about a hospital employee—a staff worker. In this embodiment, the card will hereinafter be called a "staff card." Second, the card is a database containing identifying and other information about a patient at the hospital. In this embodiment, the card will be called a "patient card."

A patient card should include information such as the patient's name, address and telephone number, her age and blood group, an indication of any chronic condition from which she suffers and any allergies that she may have. In addition it should indicate the name and address of her personal physician, the date of her most recent tetanus shot, and the identity and dosage schedule of any prescribed medicine. For most patients, all of this information may be recorded in 2 k bytes of storage. For cards having internal memory, this data may be stored on the card itself. For cards having only external memory, this data may be stored in a database which is indexed using information stored on the card. This data base may be located in a computer near the patient's bed or in a centrally located main computer. In this configuration, the patient card, like the staff card, only includes identification information, which may be used to access the remaining patient information from the local or main computer.

As shown in FIG. 1b, it is contemplated that the card may also include auxiliary storage such as a laser recording medium. This storage may be used to hold digitally compressed radiographic images or other data that cannot feasibly be stored in the card memory.

Figure 1D:
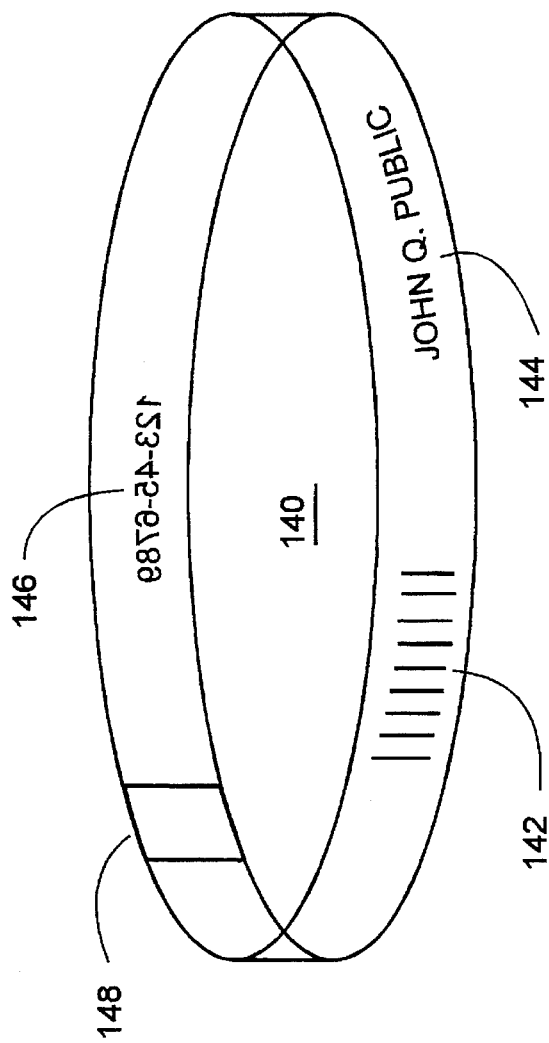
FIG. 1d is a perspective drawing of a patient wrist band.

One useful piece of information that may be stored in the card is a bar-code ID number. This number is stored onto the card from a bracelet that is attached to the patient so that it is difficult to remove. An exemplary bracelet of this type is shown in FIG. 1d. The bracelet 140 also includes the patient's name, 144, and ID number 146. The bracelet is configured to be closed, using a clamp 148, around the wrist or ankle of the patient so that it cannot be slipped over the patient's hand or foot, respectively. The use of the bar-code information is described below in reference to FIGS. 9 and 20e.

Figure 1C:
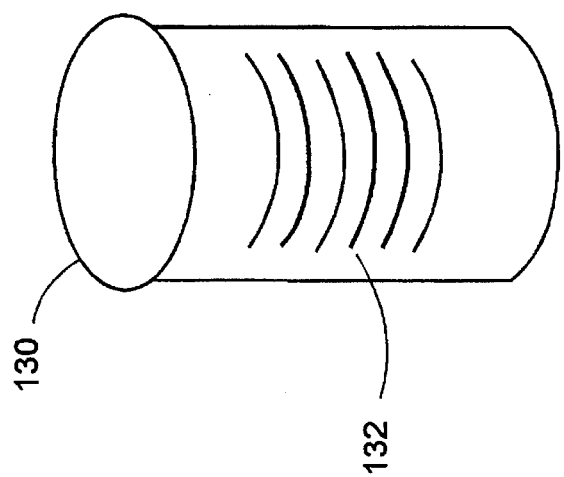
FIG. 1c is a perspective drawing of a medicine container.

Another component of the system is a bar-code 132 that is placed on medication containers 130, as shown in FIG. 1c. This bar-code is used, as described below in reference to FIGS. 9 and 20e to identify medicines to the central computer to ensure that the proper medicine is being administered to the patient and to audit the use of controlled substances in the hospital.

FIGS. 11a and 11b illustrate a mobile interface suitable for use With a staff card. This interface includes both an infra-red (IR) transmitter and a radio frequency transmitter which can transmit data to one of a group of stationary receivers or transceivers located at various places in the hospital. Transmitters and receivers suitable for use with the present invention are available from Wilton Industries of Connecticut.

The database interface shown in FIGS. 11a and 11b is a card holder 1111 which, when enabled by a base unit, converts a staff card 110' into an identification badge. The interface includes a clear plastic front piece, 1110, which protects the memory card 110' and through which information printed on the front of the card may be seen. The front piece 1110 is attached to a holder 1112 which includes all of the electronic components of the database interface. The base includes a fastener 1116, shown in the exemplary embodiment as a safety pin, which is used to attach the card holder to an article of clothing, such as the sleeve or pocket of a nurse's uniform.

The memory card 110' is inserted into a slot 1114 in the holder 1112 to make physical contact with the holder 1112. If a memory card 110' having internal memory is used, it may also make electrical contact with the holder 1112. The holder 1112 includes a push-button switch 1118 through which the person wearing the badge may signal a response to the stationary system or activate an emergency transmission mode.

When disabled, card holder 1111 cannot cooperate with staff card 1110 to form an entity capable of transmitting an identification signal. A base unit, shown in FIG. 22, enables card holder 1111 by reading data from staff card 1110 and programming it to card holder 1111. This permits card holder 1111 to cooperate with staff card 1110 to form an entity capable of transmitting identification information.

As shown in FIG. 22 base unit 2210 has a slot 2214, through which staff card 110' may be passed. Transducers located along slot 2214 read data from staff card 110' and writes it into memory in the card holder 1111 by means of a programming unit 2212. Unit 2212 is located in the base unit 2210 and is electrically coupled to card holder 1111 which will be next removed from the base unit 2210.

The base unit may be rectangular in shape and may contain one or many card holders 1111. However, only one card holder at a time is programmed with the information from a staff card 110. After card holder 1111 is programmed with the data from the staff card 110', an individual may easily remove it from base unit 2210 and couple it to the card 110' by inserting the card into the slot 1114, shown in FIG. 11. In the exemplary embodiment of the invention, if the card 110' is not inserted within 45 seconds of when the holder 1111 is removed from the base unit, the card holder will become inactive and will, instead, emit a periodic tone pulse to indicate that the card holder is inactive.

As shown in FIG. 22, the base unit may also include a key pad 2218 and screen 2220. The screen provides instructions for the user and the keypad adds security to the system by requesting a personal identification number (PIN) before programming the card holder 1111.

Prior to inserting a staff card into slot 2214, screen 2220 reads: "Slide card through slot," or a similar message. After sliding staff card 110 through slot 2214, screen 2220 may prompt for a PIN. In response to this message, the individual enters his or her personal identification number. Only if the entered personal identification number matches the personal identification number stored on staff card 110 and, optionally, in the central computer, will base unit 2210 impart the data from the staff card to card holder 1111 and activate the holder.

If the entered PIN does not match the PIN read from the staff card, an alarm may be sounded and the information from the card may not be programmed onto the card holder. In this way, the likelihood that an unauthorized person could use a stolen staff card is decreased and the security of the apparatus is increased. To prevent unnecessary alarms, it may be desirable to sound the alarm only after the individual has entered an incorrect wrong PIN a number of times in succession. Alternatively, instead of sounding an alarm, the base unit may be designed to automatically transfer the card from the programming slot 2214 to a secure holding area (not shown) when the individual has failed to provide a correct PIN after a number of attempts.

When the programmed staff card holder 1111 is has been mated to the staff card 110', the result is an entity capable of continually transmitting an identification signal. This signal is transmitted to receiver or transceiver units located in fixed locations each open area or room of the hospital. These units are electronically coupled to a central computer to form a network. Using this system, medical staff can quickly and easily be located, as described below with reference to FIG. 17c.

The exemplary card holder 1111 includes an internal switch (not shown) which is activated when the memory card 210 is inserted. Responsive to this switch, the card holder will remain enabled for up to 9 hours after the card is inserted. The holder will be disabled, however, if the card is removed and, so, the switch is deactivated for a period of at least 45 seconds. Whenever the card holder 1111 is disabled, for the reasons described above or because its internal battery is failing, it emits a periodic tone pulse through the speaker 1120, shown in FIG. 11b, to alert the wearer that a new card holder must be obtained.

Figure 4:
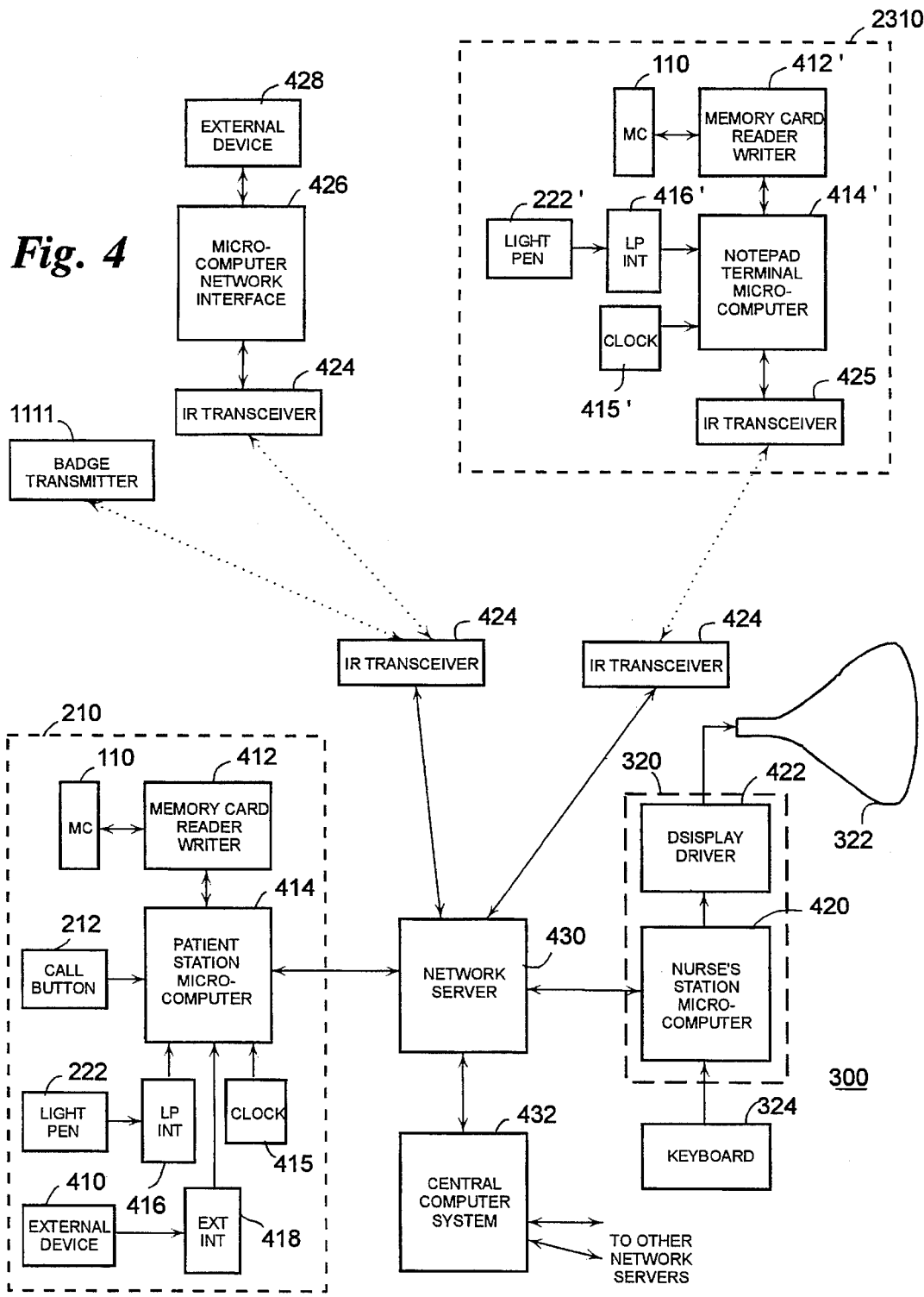
FIG. 4 is a block diagram showing the functional connectivity of the patient station and central nurse station shown in FIGS. 2 and 3.

As the enabled identification badge continually transmits its identification signal, it can be particularly useful as a locating device. For use as a locating device, the identification badge is linked by some means to a central computer. As shown in FIG. 4, identification badge transmitter 1111 sends signals to a fixed receiver or transceiver 424 which is in communication with a central computer 432 through a network server 432. This configuration is described in more detail below. For this aspect of the invention, however, it is only important to realize that identification badges 1111 are in communication with the central computer 432.

An exemplary configuration for the patient's patient station is shown in FIG. 2. The exemplary patient station 210 includes a slot 216 into which the memory card 110, preferably a patient card, may be inserted and a squeeze bulb 212, which, when squeezed, alerts the duty nurse at the central nurse station that the person in the bed needs assistance. In addition, the patient station may include a speaker 214 through which the duty nurse may both talk to and listen to the patient, push button switches 218, one of which may be used to cancel a call, a light pen 222 for reading the bar-codes such as those on the wrist band and on the medication, one or more external data inputs 220 which may be used to supply vital sign data to the central nurse station.

Figure 3:
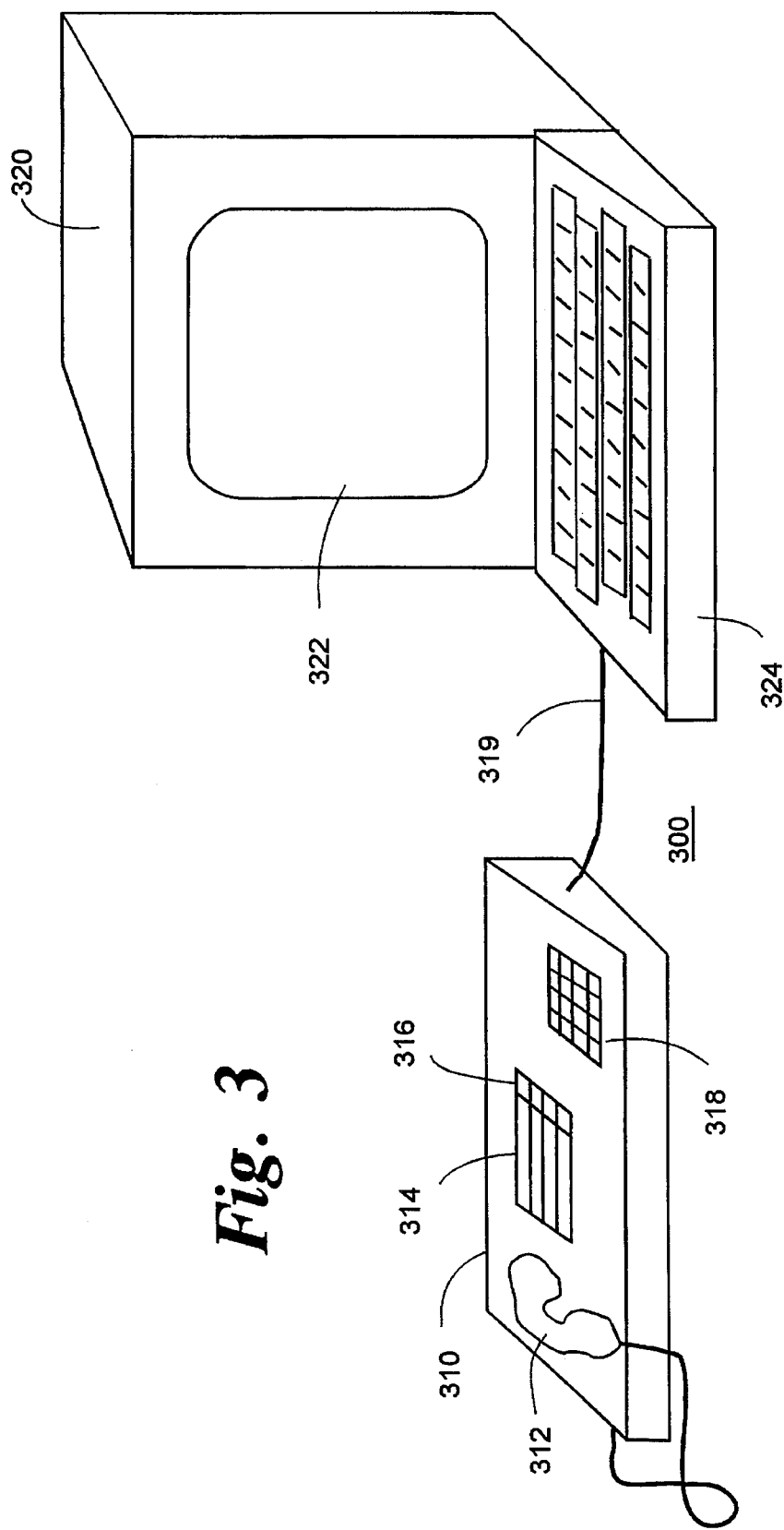
FIG. 3 is a perspective drawing of a central nurse station suitable for use with the present invention.

An exemplary central nurse station 300 is illustrated in FIG. 3. The central component of the nurse station is a microcomputer terminal 320. This may be, for example, a conventional IBM compatible personal computer.

Data indicating, for example, which patients have called and their relevant vital signs may be displayed on a video screen 322 of the microcomputer 320. Patient data, such as prescribed medication or dietary menu choices, may be entered into the central computer using the keyboard 324 of the microcomputer terminal 320. As set forth below, this data may also be stored locally at the patient station or, depending on the type of memory card used, stored in the patient's memory card.

An exemplary nurse notepad terminal is illustrated in FIG. 23. Nurse notepad 2710 includes an internal microcomputer (not shown) and an IR transceiver (not shown). Referring to FIG. 4, the notepad terminal is capable of communicating with computer 432 via the fixed transceivers located in each room of and the network servers 430 located in each floor or in each wing of each floor of the hospital.

The notepad terminal 2310 includes a slot 2314 for accepting and reading a patient card 110. As patient card 110 is slid along slot 2314, the identification and other information is read from the card and stored in the nurse notepad terminal. Clasp 2318 is a temporary holder for patient card 110. Patient card 110 is kept falling out or being confused with another by clasp 2318. Also, clasp 2318 is configured to display the individual's name 114 on the card to an operator while the card is engaged by notepad 2310.

As shown, notepad terminal 2310 includes a light-pen input device 2328. A user, such as a caregiver uses the terminal by touching the light-pen to various icons located on screen 2324. The pen 2328 is connected to the notepad by a cord 2332. The icons may include, for example, various instructions, such as obtain blood pressure, obtain time of next medication, etc. Touching icons and selecting items from menus causes the notepad unit to generate messages for the central computer 432, shown in FIG. 4, to a patient station and/or to a central nurse station. These messages are received for and sent to the network via the fixed transceivers 424 via the internal IR transceivers 425 of the notepad terminal 2710.

In one embodiment, the nurse may enters various information regarding the patient using notepad 2710. After passing patient card 110 through slot 2714, a nurse may then input such information as age, weight, smoking habits, blood pressure, cholesterol, etc. This information is then communicated to central computer 432 by being transmitted from transceiver 425 to one of the fixed transceivers 424 located in each room of the hospital and from the fixed transceivers through the network to the network server 430 and central computer 432. The fixed transceivers 424, network servers 430 and central computer 432 are linked in a hierarchical network. In the exemplary embodiment of the invention, this network operates according to a token-bus protocol such that each level controls a token which is used for communication with devices at lower levels.

Although FIG. 23 shows a light pen for communicating with the notepad terminal, it is contemplated that other means such as a keypad 2334 or a voice recognition system (not shown) could be used to enter information into the notepad terminal.

FIG. 4 is a block diagram which illustrates the functional interconnection of the various items illustrated in FIGS. 1a, 1b, 2, 3, and 23. As shown in FIG. 4, the patient station 210 includes a memory card reader/writer, 412, into which the memory card 110 may be inserted. The reader/writer 412, which may be, for example, the PC3™ memory card reader/writer available from PC3 Inc. is coupled to a patient station microcomputer 414 by a two-way data link.

The microcomputer 414 used in the exemplary embodiment of the invention uses an 80C50 microcontroller, manufactured by Intel Corp. This device includes a read only memory (ROM) program storage and random access memory (RAM) for temporary data storage. This internal memory may be augmented with external memory (not shown) The nurse call button 212 is coupled to a serial data input port of the microcomputer 414. The light pen 222 is coupled to the microcomputer 414 through a light pen interface circuit 416. A light pen interface circuit suitable for use in the patient station 210 is the PC E-Z-Reader™ 300/5G111 model available from PC E-Z-Reader Inc.

One or more external devices, such as an electrocardiogram, blood pressure monitor or respiration monitor may be coupled to the microcomputer 414 through separate external interface circuits 418. The type of external interface circuit used depends on the type of device which is to be monitored. If the device includes a standard data interface, such as an RS232 port or an IEEE 488 port, the external interface 418 may be one of the serial interface ports to the microcomputer 414. If, however, the external device 410 can only provide an analog output signal, the external interface circuit 418 may include apparatus such as an analog-to-digital converter (ADC) (not shown) to develop digital samples representing the analog waveform.

In the exemplary embodiment of the invention, digital samples of the data to be monitored are stored in a circular buffer implemented in the memory of the microcontroller 414 or in the memory card 110 itself. The number of bytes in the buffer may be fixed at, for example, 1024 and byte address may be generated using a modulo 1024 counter. Thus, new data is continually overwriting old data. In this configuration, each circular buffer holds samples representing a fixed time interval. If, for example, the buffer is limited to 1024 bytes and one-byte samples are added to the buffer at a rate of 16 per second, the stored samples represent a period of approximately one minute.

Three items of information are maintained in the fixed data portion of each circular buffer: the type of data in the buffer, the starting address of the buffer and the address of the oldest sample in the buffer. The exact format of these data items depends on the number of different types of data that may be recorded and the size of the circular buffers.

In addition to the circuitry shown in FIG. 4, it is contemplated that the patient station microcomputer 414 may be coupled to a keyboard (not shown) and to a video display monitor (not shown) so that data on the patient may be viewed from and entered into both the central computer system 432 and the memory card 110 from the patient's bedside.

Figure 14:
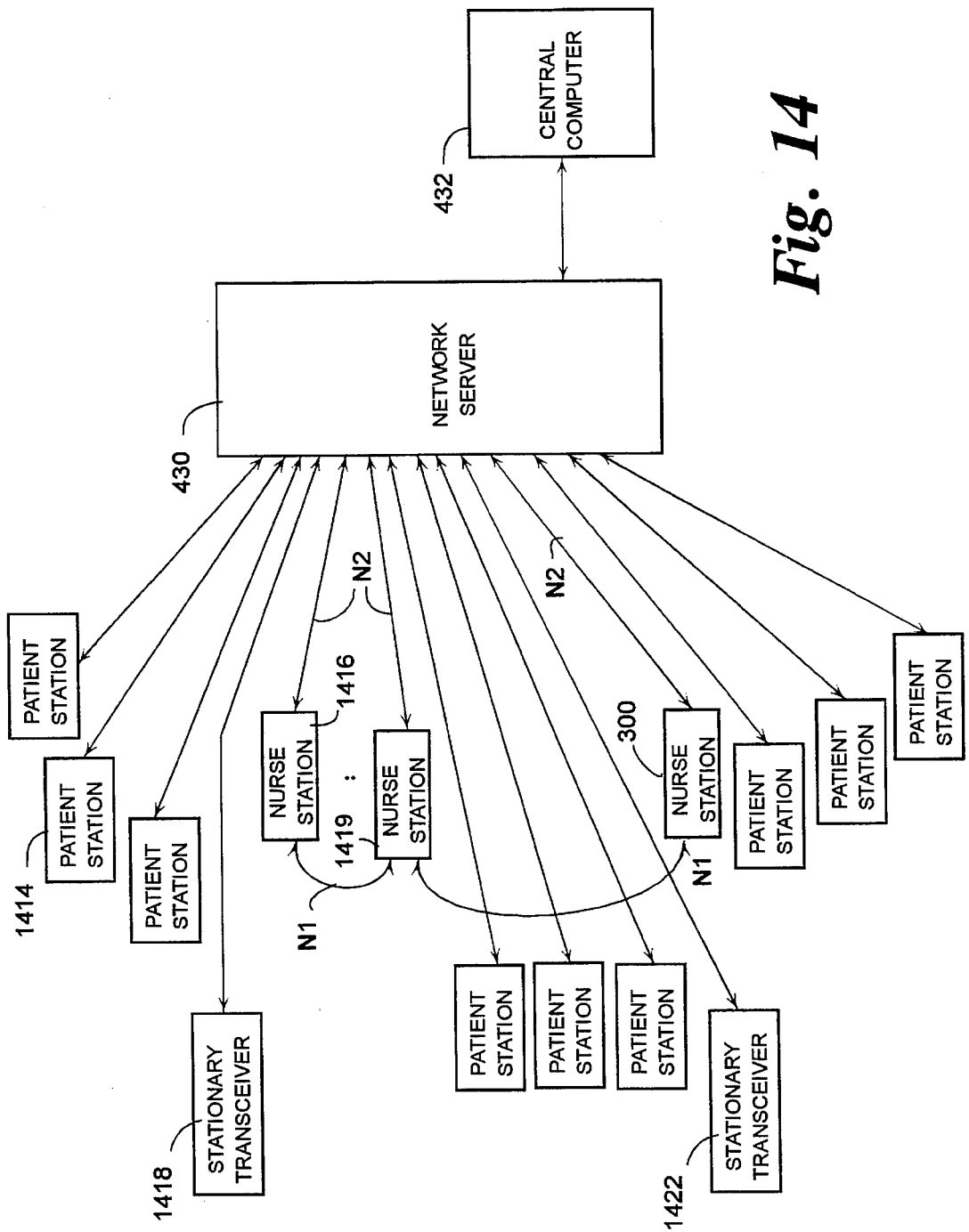
FIG. 14 is a block diagram showing an exemplary data and voice communication network suitable for use with the present invention.

The patient station microcomputer 414 is coupled to the central nurse station microcomputer 420 via a network server 430. The nurse and patient stations may be connected in a star configuration, as shown in FIG. 4, and/or in a ring configuration as shown in FIG. 14, described below. Alternatively, the patient station and the central nurse station 300 may be coupled through the telephone set in the patient's room. For this type of coupling, the network interface ports in each of the microcomputers 414 and 420 are configured to time-division multiplex data with voice communication when the telephone is in use. Multiple patient stations (not shown) may be coupled to the microcomputer 420 of the nurse station 300 via the network interconnection.

The network server 430 used to couple the patient station 210 to the central nurse station 300 may be a complex commercially available network interface such as that produced by Novell, Inc.

Portable nurse unit 2310, as shown in FIG. 23 and FIG. 4 is capable of transmitting data to a transceiver 424. There are actually a plurality of transceivers 424 throughout a hospital. In the exemplary embodiment of the invention, these are infrared transceivers capable of both transmitting and receiving infrared signals. Such infrared transceivers are desirably located in every open area of the hospital because a partition or wall can easily block an infrared signal. In general, one transceiver per room may be sufficient; however, if a room is partitioned, then it may be desirable to place one transceiver 424 in each open area of the room to easily receive the infrared transmission from external devices or nurse notepad terminals.

Transceiver 424 is in electrical communication with server 430, as shown in FIG. 4. All of servers 430 are connected, for example, in a star configuration and linked to central computing system 432.

Similarly, patient station microcomputer 414 and nurse station microcomputer 420 are linked to server 430. The patient station microcomputer 414 could either be linked by a cable or could be linked via infrared transceivers 452 and 456 in the same way that portable nurse unit 2310 is linked via transceivers 425 and 424.

The IR transceivers 424 also provide network connections for stand-alone external devices which may be used to send data on patient vital signs to the computer network and for the staff badge transmitters 1111, described above.

Figure 5:
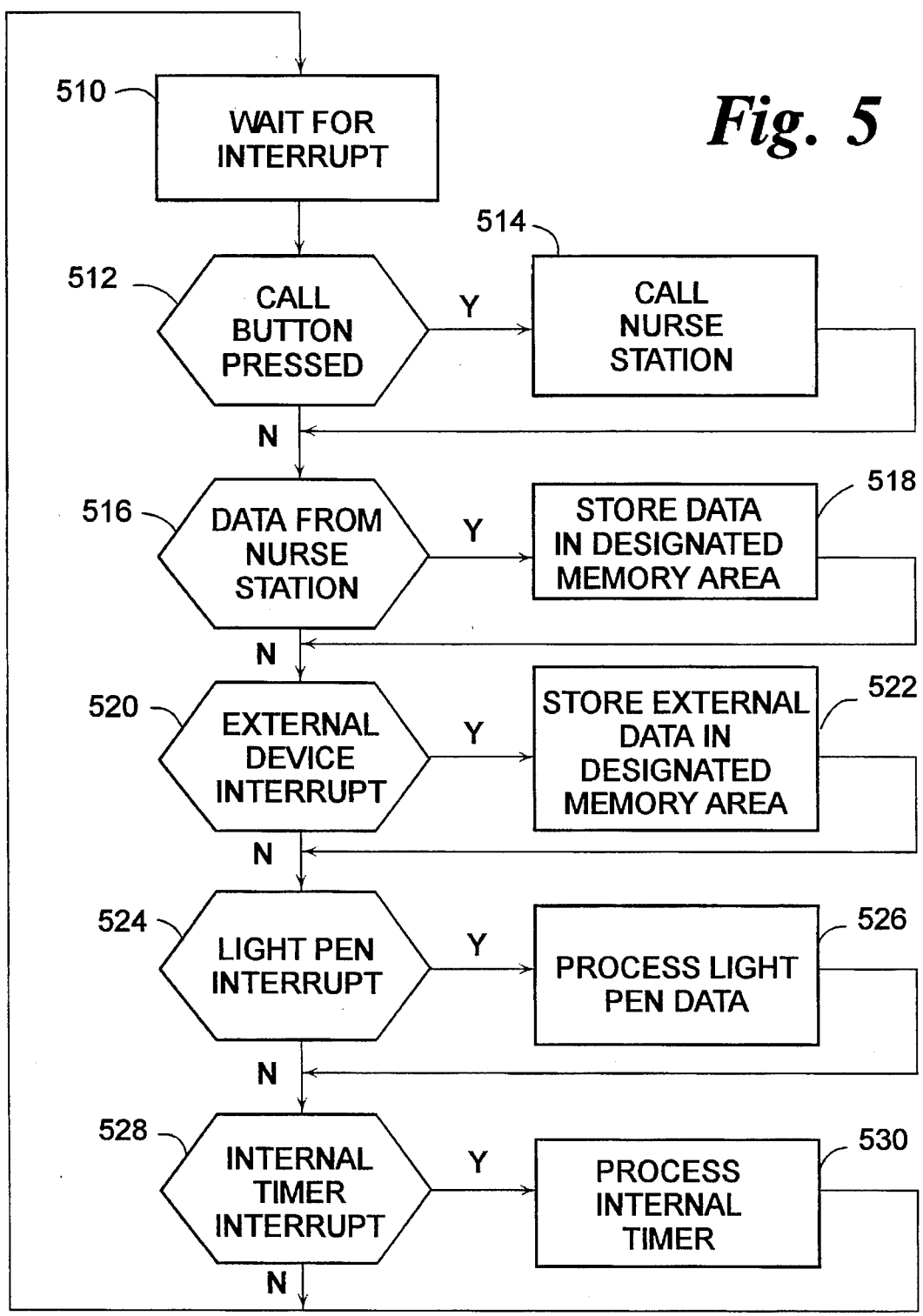

FIG. 5 is a flow-chart diagram which illustrates the main loop of the program that controls the patient station 210. At step 510, the microcomputer 414 in the patient station 210 is in an idle state waiting for an interrupt. In this state, the microcomputer 414 may be used for other purposes, such as to provide the patient with information or entertainment. Alternatively, the microcomputer 414 may be programmed with diagnostic aids for use by the caregivers in monitoring the patient's condition.

When an interrupt occurs, the computer 414 enters an interrupt routine which checks for the occurrence of each possible type of interrupt, processes the interrupts which have been provided to the routine and returns the microcomputer 414 to its idle state.

At step 512, the interrupt routine determines if the interrupt was generated by the patient squeezing the bulb 212 or by pressing the nurse call button. If so, the step 514 is executed which performs the call nurse station function and control is transferred to step 516. The steps which implement the call nurse station function are described below with reference to FIG. 6.

After the nurse call interrupt is processed at step 514 or if the interrupt was not a nurse call at step 512, the interrupt routine, at step 516, determines if the interrupt was caused by data being provided to the microcomputer 414 from the central nurse station 300. If so, step 516 invokes step 518 to store the data provided from the nurse station 300 into the local memory of the patient station or, if appropriate, into the memory card 110 itself. Step 518 and then transfers control to step 520. The steps which implement the step 518 are described below in reference to FIG. 7.

If, at step 516, it is determined that the interrupt was not caused by the receipt of data from the nurse station 300, control is transferred to step 520. Step 520 determines if the interrupt was generated by an external device, coupled to the external device input port 220 (shown in FIG. 2). As set forth above, one or more external devices may be coupled to the patient station 210 to store a vital sign data in its local memory or on the memory card 110. The interrupt detected at step 520 would occur when one of these external devices is ready to provide a sample to the patient station 210.

If step 520 determines that the interrupt is from an external device, step 522 is executed to store the external data onto the card and then control is passed to step 524. The process represented by step 522 is described below with reference to FIG. 8.

If, at step 520, it is determined that the interrupt was not generated by an external device, control is transferred to step 524. Step 524 is executed to determine if the interrupt was generated by the light pen 222. As set forth above, the light pen 222 is provided to read bar-coded information from patient wrist bands, containers of prescription medicine, food trays, diagnostic images and other material that is desirably associated with a particular patient. the light pen 222 may be operated, for example, by pressing a button on the pen while the pen is dragged across the bar code and then releasing the button. The light pen interrupt would be generated when the button is released. If a light pen interrupt is detected at step 524, the interrupt routine invokes step 526 to process the light pen interrupt and then transfers control to step 528. The steps performed in carrying out step 526 are described below with reference to FIG. 9.

If, at step 524, it is determined that the interrupt was not generated by the light pen 222, control is transferred to step 528. Step 528 determines if the interrupt was caused by the internal timer of the microcomputer 414. If so, step 528 invokes a step 530 to process the internal timer interrupt. This step acts as an alarm clock to ensure that medication is administered on time and to ensure that any data which needs to be monitored at timed intervals is handled properly. When the internal timer has been processed, step 530 transfers control to step 510 to wait for the next interrupt. Control is also transferred to step 510 from step 528 if it is determined that no internal timer interrupt needs to be serviced.

In this description of the exemplary embodiments of the invention, reference is made to storing data into the card. If either of the memory cards 110 and 110' has limited or external memory or has internal memory which can undergo only a limited number of storage operations, it may be desirable to assign a buffer area in any of the microcomputers or microcontrollers coupled to the data card which acts as the card memory while the card is coupled to the device. In this instance a write operation to memory locations on the card would only be made when the card is removed from the device. At this time, the contents of the buffer may be transferred to the memory card as a block or separate write operations may be performed for those locations that have been changed while the card has been attached to the device.

Figure 6:
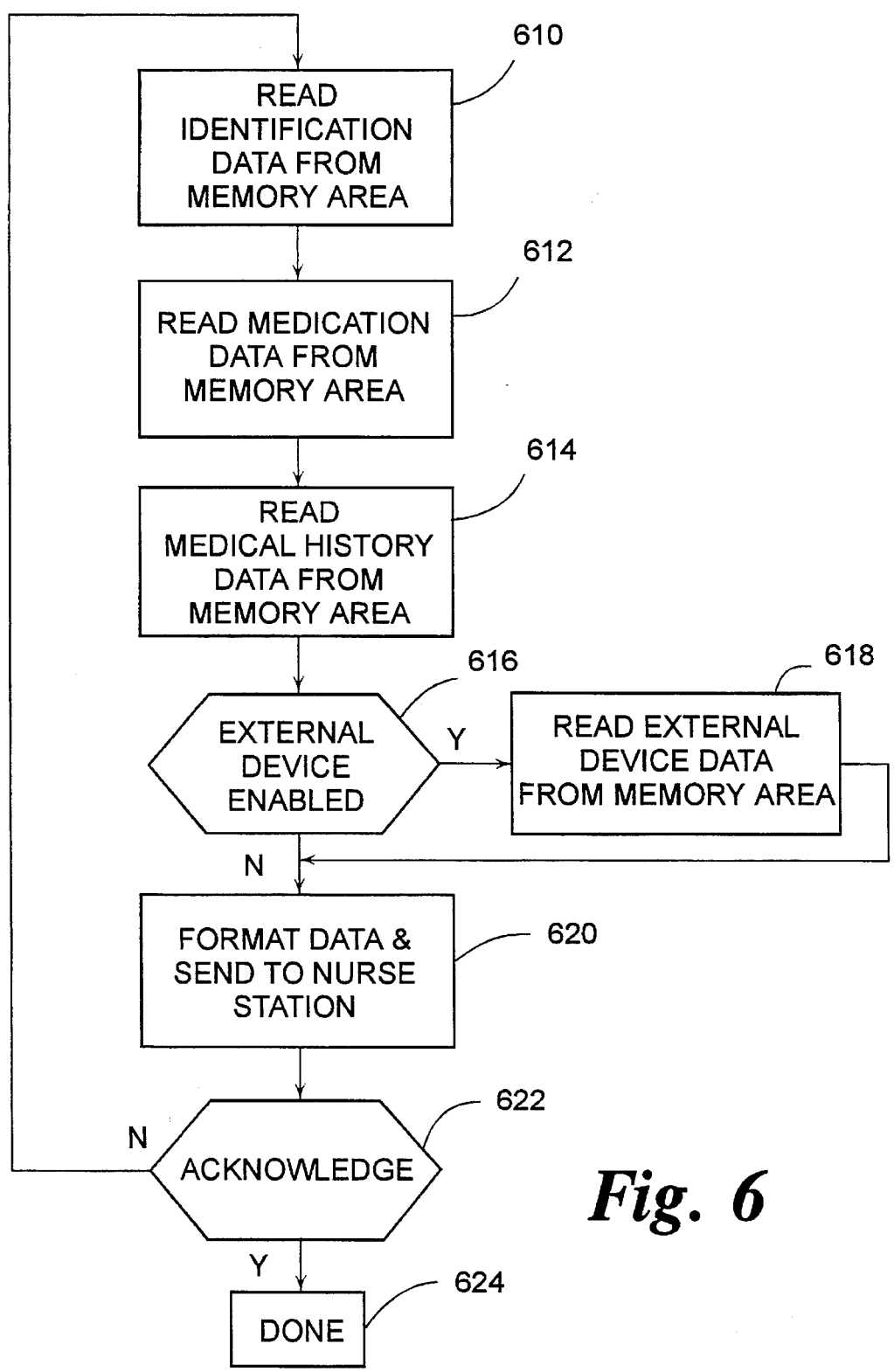

FIG. 6 is a flow-chart diagram showing details of the processing steps performed by the processor 414 in response to a nurse call interrupt. Steps 610, 612 and 614 read fixed data from the patient station 210 as shown in FIG. 2. This data is stored in the local memory of the computer 414. At step 616, the microcomputer 414 determines if an external device is coupled to the external device input port 220, if the patient station 210 has been enabled to receive data from the device and if the device has written any data to the patient station memory. If all of these conditions are met, step 616 transfers control to step 618. The microcomputer 414, at step 618, determines the location of the data to be read and the address of the oldest sample.

After step 618, or if one of the conditions fails at step 616, control is transferred to step 620. This step formats the data that is to be transferred to the nurse station 300 and transmits it to the nurse station via the network server 430.

At step 622, the microcomputer 414 waits for an acknowledge (ACK) response from the microcomputer 420. If a negative acknowledge (NAK) is received or if there is no response after a predetermined time-out period, the computer 414 transfers control back to step 610 and the process of extracting, formatting and transmitting the data is repeated. If the ACK is received at step 622, the call nurse station process terminates at step 624. The nurse call message remains active at the nurse station 300 until it is cleared by pressing the CLEAR button 218 of the patient station 210, as shown in FIG. 2.

Figure 7:
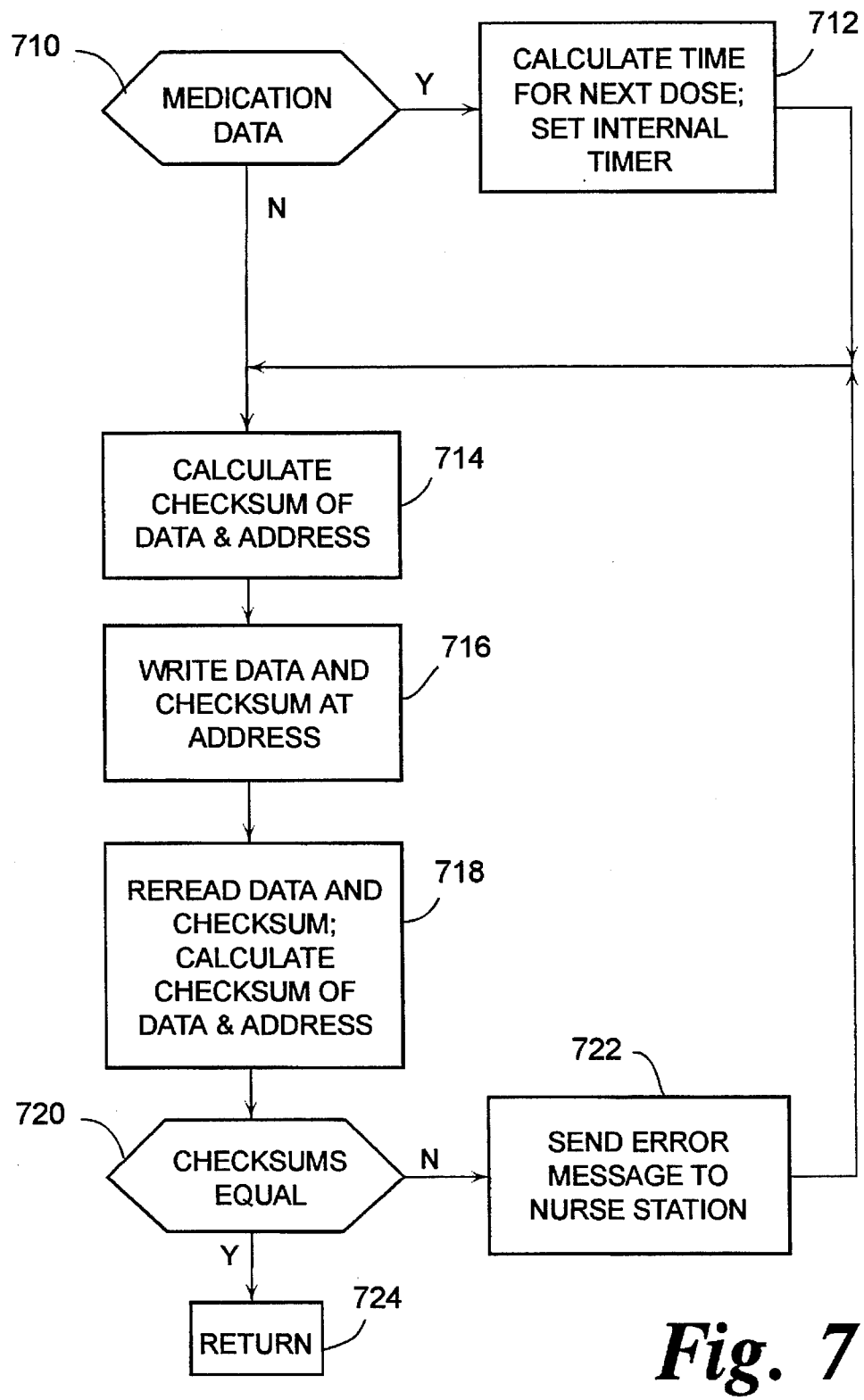

FIG. 7 illustrates the program flow of the process which stores data onto the memory card or into the memory card buffer area of the microcomputer 414. This process is step 518 of FIG. 5. The first step in the process, step 710, determines if the data being entered is medication data. If so, at step 712, the process calculates the time for the next dose and sets the interval timer.

After step 712 or if the data is not medication data at step 710, the process executes step 714, which calculates a checksum of the data and the address at which the data is to be stored. At step 716, the data and the checksum are then supplied to the memory card buffer area or to the memory card reader/writer 412. The data is provided with the starting address on the card of the first storage location to be used to hold the data. Step 716 also conditions the reader/writer 412 to write the data onto the card.

At step 718, the microcomputer 414 conditions to read the data that was just written to the card or to the card buffer area and calculates a checksum for the data and address value. Step 720 compares the checksum calculated for the original data to the checksum calculated for the retrieved data. If the checksums are not equal, the microcomputer, at step 722, sends an error message to the nurse station microcomputer 420 and transfers control to step 714 to retry the data storage operation. If, at step 720, the checksums are found to be equal, the data storage process terminates at step 724.

Figure 8:
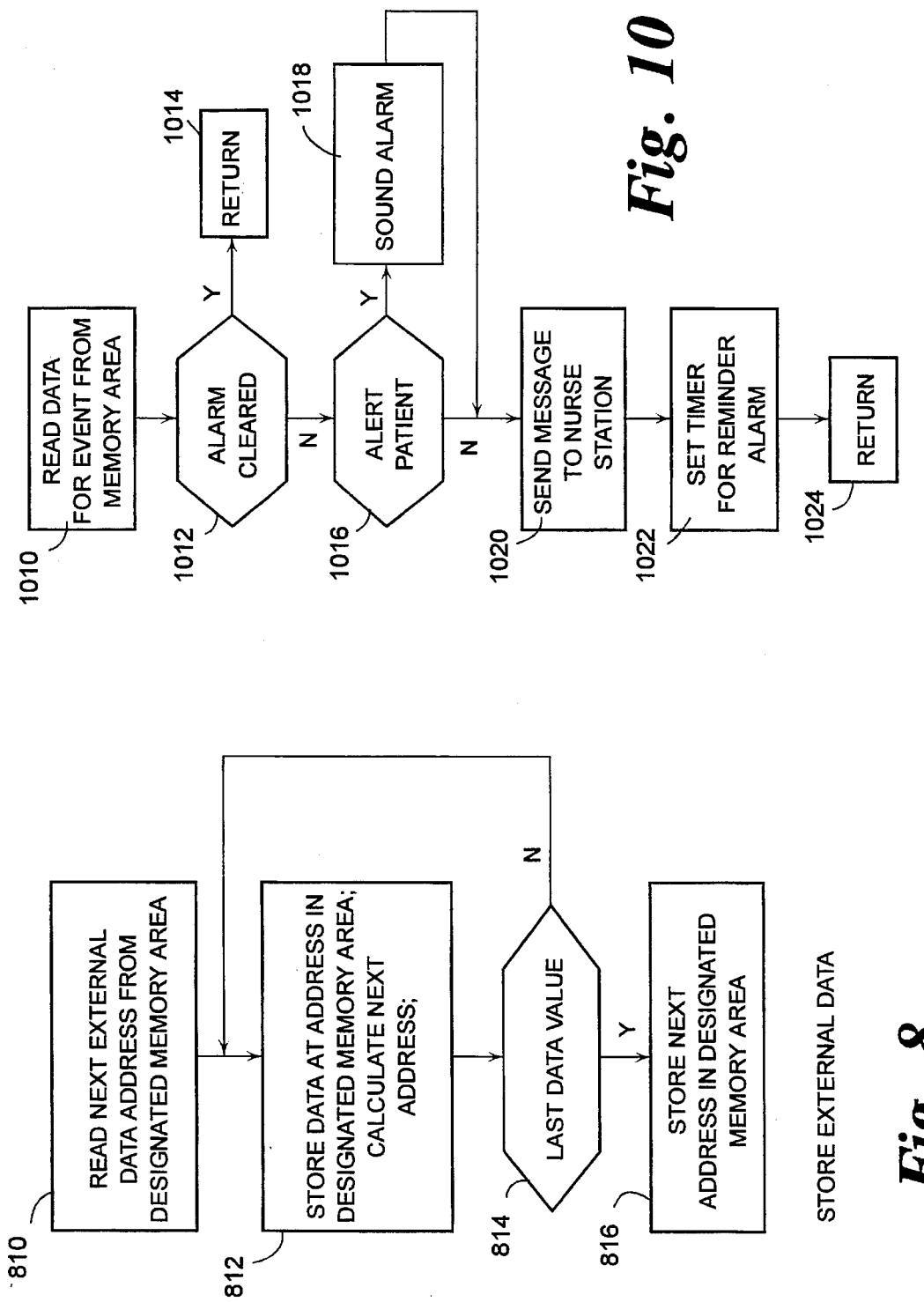

FIG. 8 is a flow-chart diagram of the process 522 of FIG. 5, which stores data from external devices into the local memory of the patient station microcomputer 414. The first step in the process, 810, reads the next data address into which data is to be written from the card buffer area in the microcomputer 414. This address is the same as the address of the oldest data item. Step 812, stores one byte of data into this address and calculates the next address. As set forth above, the address calculation uses the length of the buffer as a modulus so that the buffer appears to be a circular buffer. For example, if a buffer length of 1024 is selected and the base address of the data in the local memory of the microcomputer 414 is at BASEADR, the address calculation to obtain the next address, NXADR from the current address, CURADR may be calculated using the equation (1).

$$NXADR=BASEADR+(CURADR-BASEADR+1) \text{ modulo } 1024 \quad (1)$$

At step 814, the microcomputer 414 determines if the data item just stored was the last data item to be processed. If so, step 816 is executed in which the microcomputer 414 stores the calculated next address value in the memory card buffer area as the address of the oldest data item. Step 816 then ends the external data storage process. Otherwise, step 814 transfers control to step 812 to write the next data item onto the designated card buffer area.

In the same way that external data is stored from patient station microcomputer 414, data can be stored from portable nurse unit 2310. Such data could be entered from an external device with a transceiver 411. This information is communicated to the portable nurse unit then sent by transceivers 425 and 424 to server 430. The information could either be stored at server 430 or server 430 could be configured to send a signal back through transceivers 424 and 425 to the portable nurse unit 2310 instructing the nurse unit to impart the information onto the memory card which is loaded onto the portable nurse unit.

Figure 9:
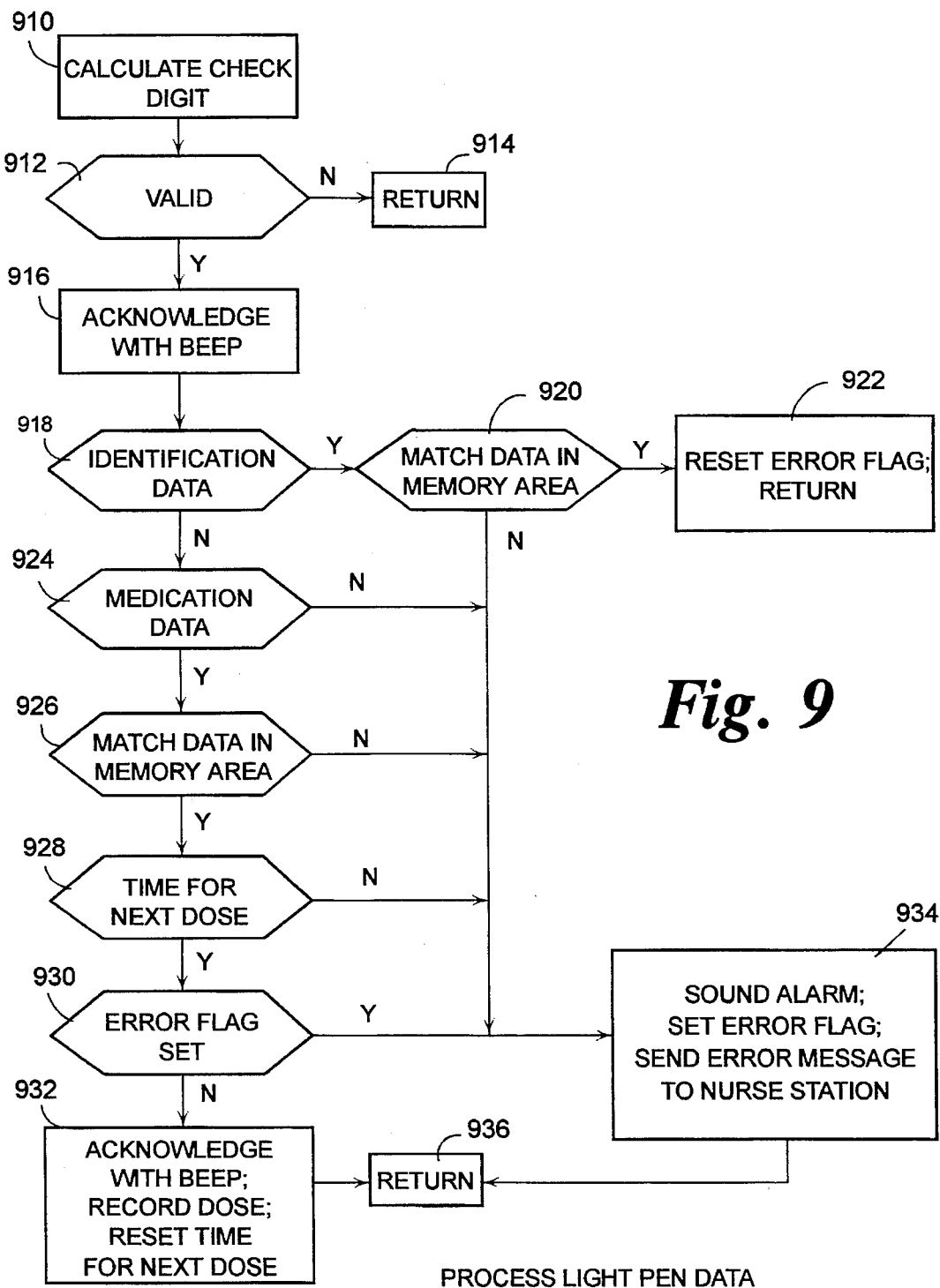

FIG. 9 illustrates the steps performed by the microcomputer 414 in processing data from the light pen 222 of FIG. 2. In the exemplary embodiment of the invention, the light pen data is provided to the microcomputer 414 via the light pen interface 416, shown in FIG. 4. This interface translates the alternating light and dark patterns sensed by the light pen 222 into a sequence of digits. Conventional bar-coded data includes a check digit, such as a cyclic redundancy code (CRC) digit, as the last digit of the data. This digit may be calculated by applying a predetermined formula to the other bar-coded digits.

In the exemplary embodiment of the invention, bar-codes are used to ensure that medications, radiographic images, food trays and other material are provided to the proper patient. As an example of how the bar-codes may be used for this function, consider the administration of prescribed medication. Before giving the medication to the patient, the nurse first scans the patient arm band. The patient station compares the scanned data to the identification data retrieved from the card. If these two codes do not match then either the patient is in the wrong bed or the wrong memory card is inserted in the patient station 210.

If the codes do match, the nurse then scans the bar-code on the medication container. The patient station 210 compares the scanned data to medication data in the memory card buffer area. If a match is found, the station 210 determines when the next dose of the medicine is to be administered. If the next dose is past due or if it is due in the near future, the patient station 210 records the time at which the medication was given. If the medication is not found in the card buffer area or if it is not yet due, the station 210 sounds an alarm, for example a distinctive series of pulse tones, and sends an appropriate error message to the nurse station 300. If, as set forth above, the patient station 210 is equipped with a display device, the error message may also be displayed on the patient station display.

For radiographic images, food trays and other material that is simply to be delivered to the patient's bed, a bar-code identifying the patient is scanned from the image, tray or other material. The scanned data is then compared to the identifying data on the card. If the data is correct, the scan is acknowledged with a beep. Otherwise the alarm is sounded and an error message is sent to the nurse station 300 indicating that material has been delivered to the wrong patient.

The first step in FIG. 9, step 910, calculates the check digit using all but the last digit of the code supplied by the light pen interface 416. Step 912 then compares the calculated check digit to the last digit of the scanned code. If the digits do not match, step 914 is executed which returns control to the main loop program shown in FIG. 5.

If, however, the check digit is found to be valid at step 912, step 916 is executed which acknowledges the receipt of the code by conditioning the patient station 210 to emit a beep from its speaker 214. At step 918, the microcomputer 414 determines if the code provided by the light pen interface 416 is identification data. If so, step 920 is executed to determine if the supplied code matches the code stored on the card buffer area. As set forth above, this code was entered into the buffer area from the card. The data on the card was entered by scanning the patient's arm band during admission processing. If the scanned identification code matches the stored code at step 920, step 922 is executed which resets the error flag and returns control to the main program loop.

Otherwise, step 934 is executed. This step sounds an alarm through the speaker 214 of the patient station 210, sets the error flag and sends an error message to the central nurse station 300 indicating that the scanned identification data does not match the stored data.

If, at step 918, the scanned data is not identification data, step 924 is executed. Step 924 determines if the scanned data is medication data. If so, 926 is executed, otherwise, an error has occurred and control is transferred to step 934. This step operates in the same manner as set forth above, except that the error message indicates that the scanned data was neither identification data nor medication data.

Step 926 determines if the scanned medication matches any of the medication data stored in the memory card buffer area. If a match is found, step 928 is executed, otherwise an error has occurred and step 934 is executed with an error message indicating that the medication has not been prescribed for the patient.

In step 928, the microcomputer 414 compares the current time, as derived from its internal time of day clock, to the stored time for the next dose of the medication. This time value is stored in the card buffer area as a part of a multi-value record for the medication information. Each prescribed medication is entered in the buffer area as a separate medication record. If the next-dose time has passed or if it is in the near future, for example, 15 minutes from the present, step 930 is executed. Otherwise, an error has occurred and step 934 is executed with an error message indicating that the medication is being provided at the wrong time.

Step 930 checks the error flag. This flag is set in step 934 if any error occurs and is reset in step 922 when the scanned identification data is found to match the patient. The test in 930 ensures that erroneous identification data is not ignored. If the error flag is set at step 930, then an error that occurred during a previous attempt to administer medication has not been cleared. In this instance, step 934 is executed with an error message indicating that a previous error has not been cleared.

If, at step 930, the error flag is reset, step 932 is executed. This step conditions the patient station 210 to emit an acknowledging beep, disables any internal timer interrupt that may be set for this medication dose, records the current time in the medication record to indicate that the medication has been administered and calculates the time for the next dose. The next-dose time is also stored in the medication record on the memory card buffer area of the microcomputer 414 and an internal timer interrupt is set for this next dose time. After step 932 and after step 934, the process which reads the light pen data is complete and control is returned to the main loop program at step 936.

In the same way as shown in FIG. 9, portable reader 2310, as shown in FIG. 23 and at FIG. 4, can be used in place of the combination of light pen and patient station microcomputer to determine when the next dose of a prescription drug is due. Portable reader 2310 has a slot, 2314, for accepting and scanning and reading the information from a patient memory card. It also can read a bar code on a patient's wrist or a medication bottle using a light pen 2328. Portable reader 2310 also is capable of transmitting input of this information to a fixed transceiver such as transceiver 424 as shown in FIG. 4. This information is then sent to server 430 via transceiver 425. The portable reader 2310 operates in the same manner as the patient station as illustrated by FIG. 9.

FIG. 10 illustrates the program flow of step 530 of FIG. 5, which processes the internal timer interrupts from the microcomputer 414 of the patient station. In the exemplary embodiment of the invention, the timed event, for example, the next-dose time in a medication record, is stored in the card buffer area at a known location. Step 1010 reads the event data from the buffer area, using the address that was stored with the timer interrupt request. Step 1012 compares the stored time to the current time and checks an alarm cleared flag to determine if the alarm is no longer necessary. If step 1012 determines that the alarm has been cleared, control is returned, at step 1014, to the main program loop of FIG. 5.

If the alarm has not been cleared at step 1012, step 1016 is executed to determine if the patient is to be alerted or if only the nurse station 300 is to be alerted. If the patient is to be alerted, step 1018 is executed which conditions the patient station 210 to emit an audible alarm through the speaker 214. Whether or not the patient is to be alerted, step 1020 is executed to send an alarm message to the nurse station 300. In the exemplary embodiment of the invention, the text of the alarm message is determined from a code stored with the timer interrupt data on the memory card 110. This code is used to index a table of alarm messages stored in read-only memory (ROM) (not shown) in the patient station microcomputer 414.

After step 1020, the microcomputer 414 executes step 1022 to set a reminder alarm for a predetermined time, for example, five minutes after the initial alarm. This reminder alarm is handled in the same manner as any other internal timer interrupt. Any outstanding reminder alarms may be cleared by pressing the CLEAR button 218 on the patient station 210.

The discussion above has centered on the use of the invention for patients in a hospital. Since a hospital patient spends a large percentage of time in his bed, the interface between the personal database and the hospital computer system can be a fixture in the patient's room. For reasons set forth below, it is desirable to extend the use of the invention to caregivers at the hospital. Caregivers, however, are more mobile and would not be adequately served by an immobile interface.

Figure 12:
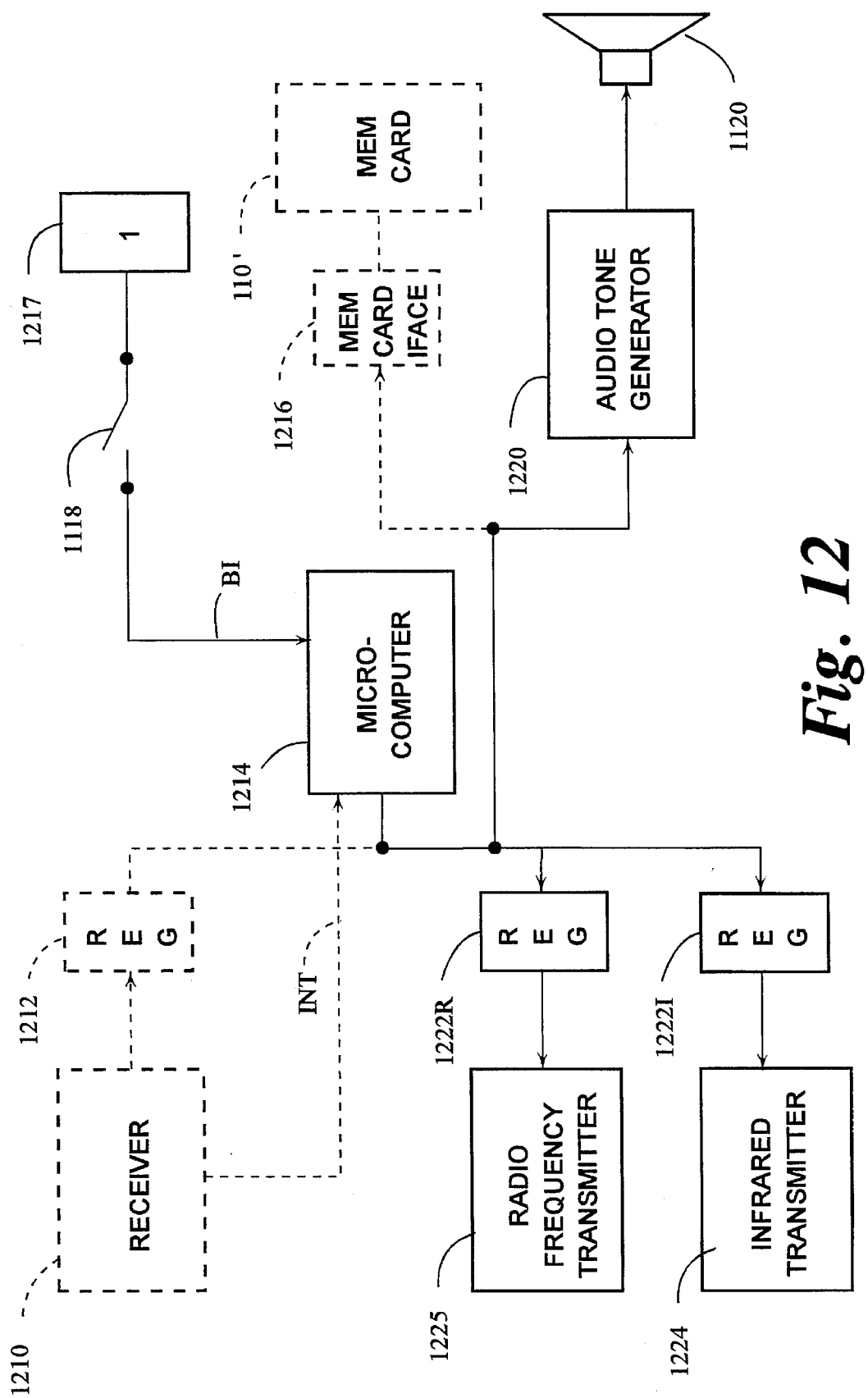
FIG. 12 is a block diagram showing the functional connectivity of the portable transceiver shown in FIGS. 11a and 11b.

FIG. 12 is a block diagram that illustrates the functional structure of the electronic circuitry in the base 1112 of the badge-holder database interface. For the sake of simplicity, the power supply has been omitted from FIG. 12. In the exemplary embodiment, power is provided by a standard replaceable lithium battery (not shown). The microcomputer 1214 may be any one of a number of commercially available microcontrollers, such as the 80C49 manufactured by Intel Corporation, coupled to ROM program storage (not shown) and RAM data storage (not shown).

The badge transmitter includes an infrared transmitter 1224, a radio frequency transmitter 1225 and an audio tone generator 1220. Badges which are able to both send and receive data and to store data into a programmable memory card also include an infrared receiver 1210 and a memory card interface 1216.

In a badge transceiver of this type, the functions performed by the microcomputer 1214 may include providing an address to a memory card interface 1216 to store data into or read data from the memory card 110, conditioning an audio tone generator 1220 to produce an audio signal from the speaker 1120, or storing a value into one of the registers 1222I and 1222R and then conditioning the appropriate transmitter 1224 or 1225 to broadcast the data value to the network of fixed infrared and RF transceivers.

Alternatively, when the badge transmitter is a simple transponder which emits an identification code at predetermined intervals as programmed by the base unit, the microcomputer 1214 may be eliminated and replaced by a programmable timer and/or simple logic circuitry to perform the limited functions of the transponding badge.

Also included in the badge circuitry is the push-button switch 1118, through which a source of logic-one value, 1217, may be momentarily coupled to an interrupt line, BI, of the microcomputer 1214. In response to this interrupt, the microcomputer 1214 sends identifying information, read from the memory card 110' and either an emergency alert message or an acknowledge message using both the infrared transmitter 1224 and the radio frequency transmitter 1225. The operation of the circuitry shown in FIG. 12 in the hospital environment is described below with reference to FIGS. 13–16.

In the exemplary embodiment, the badge holder includes two transmitters, an infrared transmitter 1224 which is used primarily to send identification data and a radio-frequency device, operating at frequencies of approximately 300 MHz. Radio frequency transmitters suitable for use in the badge holder are available from Dallas Semiconductor Inc. It is contemplated that other transmitter components may be used, for example, the infrared transmitter of the PLS-4000 personnel locating system available from TELOC, Inc.

FIG. 13 is a flow-chart diagram which illustrates the operation of the badge transmitter shown in FIGS. 11 and 12. The badge transmitter is activated by an interrupt at step 1310. The interrupt may be from the push-button switch 1118 or from an internal timer (not shown) which is set by the base unit 2210, shown in FIG. 22, to periodically transmit the identification information. If, at step 1312, it is determined that the interrupt was generated by the switch 1118, the microcomputer 1214, at step 1314, conditions the audio generator 1220 to provide a pulse tone signal to the speaker 1120. This tone serves as audio feedback letting the wearer know that the badge circuitry has sensed the closing of the switch 1118.

When the button 1118 is pushed, the wearer is assumed to be signalling an emergency alert. In this instance step 1320 is executed which conditions the microcomputer 1214 to send an emergency alert message to the transmit registers 1222I and 1222R and to transmit the message through both the IR transmitter 1224 and the RF transmitter 1225. In order to reduce the number of accidental emergency alert messages, it may be desirable to program the microcomputer 1214 to require that the switch 1118 be pressed in a pattern, for example, three times within a 10 second interval to signal an emergency alert. After the message is transmitted in step 1320, control is transferred to step 1310 to await the next interrupt. If the host computer is waiting for an acknowledgement from the badge wearer, this message is interpreted as an acknowledgement. Alternatively, it may be desirable to have another code, for example, pressing the switch once or twice to indicate an acknowledgement.

If, at step 1312, the interrupt is a timer interrupt, a signal which includes a synchronization component and an identification component is transmitted in a discrete time interval, for example 45 microseconds, at a preset time interval having a maximum length of, for example 3 seconds. As set forth above, this time interval is assigned by the base unit 2210 when the badge holder 1111 is programmed.

At step 1346, the identification data and a check sum are generated by the microcomputer 1214 and, at step 1349, are loaded into the IR transmission register 1222I. Also at step 1349, the IR transmitter 1224 is activated to transmit the data. At step 1350, the badge transmitter returns to an idle state to await the next interrupt.

The timer, which is programmed by the base unit 2210, repeatedly interrupts the badge unit at a fixed time interval which is different for each badge unit. Since an individual transmission occupies only 45 microseconds out of a three-second interval, as many as 65,536 ($2^{16}$) such intervals may be defined. This continual transmission of relatively short identification signals permits a relatively large number of entities within one communication network while keeping the likelihood of conflicts caused by overlapping message transmissions low.

As set forth above, the badge transmitter is used, in this embodiment of the invention may be used as a data link between the personal database implemented in the memory card 110' and the central computer system. The portable nurse station 2310 and external devices, such as device 428 of FIG. 4 may also be coupled to the central computer via a wireless data link. The other part of this data link is the network of stationary transmitters located at fixed positions around the hospital. FIG. 14 is a block diagram showing the data link between the network of stationary transceivers, the nurse stations, the patient stations and the central computer system 432.

As shown in FIG. 14, the stationary transceivers 1402 and 1404; the nurse stations 1406, 1408 and 1410; and the patient stations 1412 through 1428 are all coupled to the network server 430 via a star-type network N2. In addition, the nurse stations 1406, 1408 and 1410 are coupled together by a ring network N1. In the event of a failure of the central computer 432 or network server 430, data communications among the central nurse stations would occur through the network N1.

In the exemplary embodiment of the invention, each of the stationary transceivers 1402 and 1404 is responsive to commands from the central computer 432, transmitted via the network server 430, to receive identification data from (and optionally transmit data to) the various badge transceivers, to receive telemetry data from external devices such as the device 428 of FIG. 4 and to receive data from and transmit data to the portable nurse stations such as the station 2310 of FIG. 4. Each stationary transceiver includes circuitry which automatically performs all of the steps needed to ensure that the command from the main computer is carried out and that the data was delivered without corruption.

Figure 15:
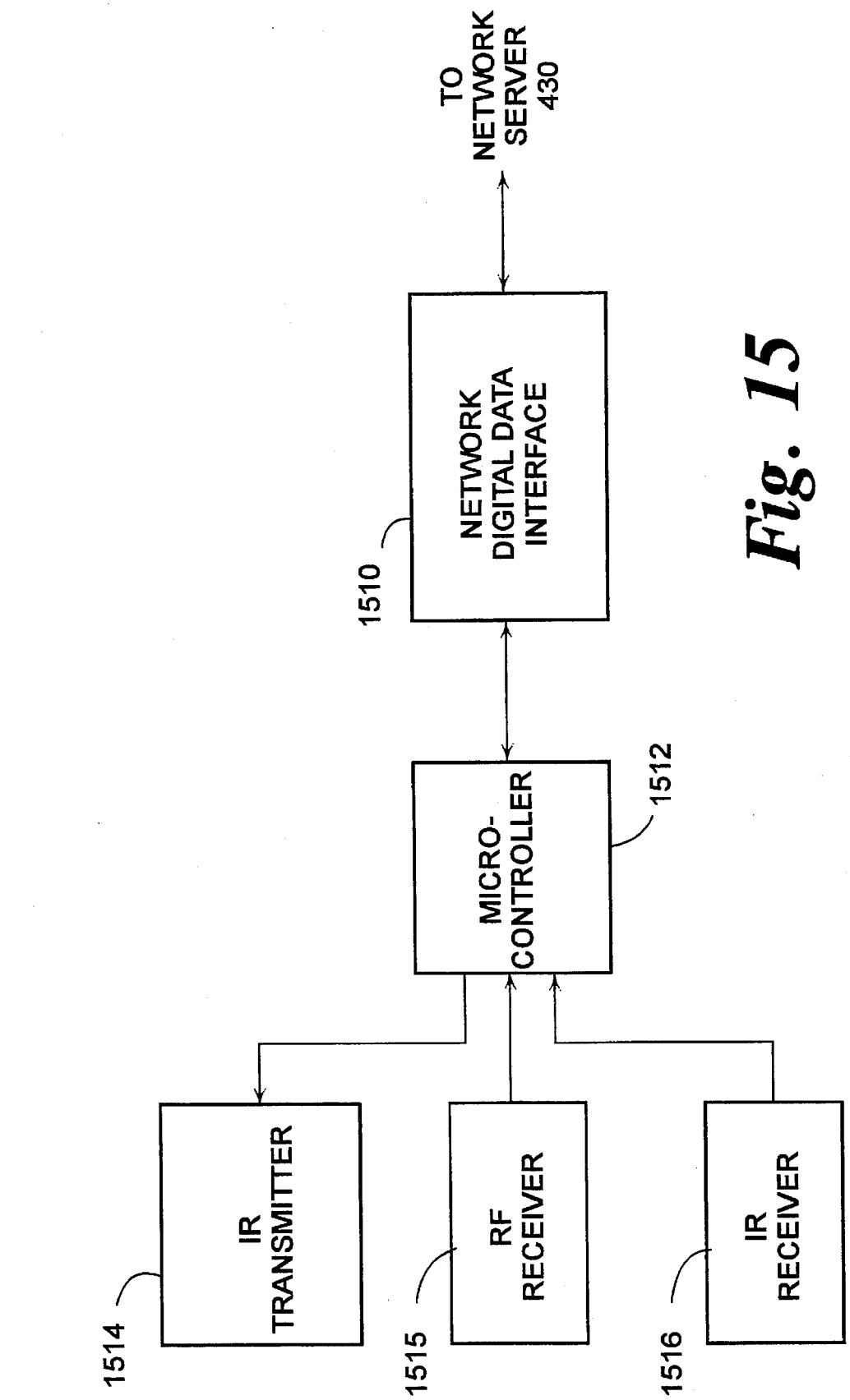
FIG. 15 is a block diagram showing details of the transmitter-receiver units shown in FIG. 14.

FIG. 15 is a block diagram showing the functional structure of a stationary transceiver. In addition to an infrared transmitter 1514, an infrared receiver 1516 and an RF receiver 1515, the transceiver includes a microcontroller 1512 and a digital data interface 1510 through which the transceiver is coupled to the server 430. The network digital data interface 1510 provides a digital data connection to the server 430. The type of unit used depends on the network connectivity available to the server.

The stationary transceiver shown in FIG. 15 includes a microcontroller 1512. This unit includes a simple microprocessor (not shown), a ROM program store (not shown) and a small RAM (not shown) for holding data and temporary results. The microcontroller 1512 is programmed to implement a low-level portion of a hierarchical token bus protocol. It supplies a token to one of FIG. 16a is a flow-chart diagram which illustrates the process steps performed by the program that controls the microcontroller 1512. As set forth above, the stationary transceivers 1418, 1422 and 1428 are programmed to carry out commands provided by the central computer system. These commands include: a status request command for which the stationary transceiver sends an indication of its status to the main computer, a transmit data command for which the stationary transceiver transmits data provided with the command, and a receive data command for which the stationary transceiver expects to receive data from a portable nurse station, external monitoring device or, optionally, a badge transceiver. Multiple commands may be issued at a single time.

At step 1604 of the stationary transceiver process, as shown in FIG. 16a, the transceiver waits for an interrupt. When an interrupt occurs, it may be from the infrared or RF receiver or it may be from the central computer 432 via the network server 430. Interrupts from the infrared or RF receivers may occur at any time. As set forth above, these interrupts may signal the receipt of an identification message sent by a transponder badge or an emergency alter message caused by pressing the emergency alert button on the badge. If, at step 1606, the message is from the IR or RF receiver, step 1608 is executed to format the message and send it to the network server 430. After step 1608, control is returned to step 1604 to await the next interrupt.

Alternatively, if, at step 1606, a message from the network interface is detected, step 1610 is executed. At step 1610, the command message is received from the central computer 432 via the data communications network N2 and the network interface 1510 and the number of commands in the message is stored in a memory location COMMAND COUNT. This memory location serves as a pointer to the commands in the message.

Step 1609 determines if any commands in the message have not been executed. If unexecuted commands exist, then at step 1611, the next command is selected from the message. At step 1612, the microcontroller 1512 determines if this command is a status request command. If so, step 1614 is executed. This step sends a status message to the central computer 432 and decrements COMMAND COUNT so that it points to the next command. The status message may include, for example, information identifying the stationary transceiver and its location, and the numbers of ACK and NAK messages both sent and received by the stationary transceiver. The relative numbers of ACK and NAK messages provide an indication of the condition of the stationary transceiver. After step 1614 control is transferred to step 1609 to extract the next command from the received message.

If, at step 1614, the selected command is not a status request, then step 1616 is executed. This step determines if the command is a transmit data command. If so, at step 1618, the data to be transmitted is sent to the infrared transmitter 1514 and the transmitter is conditioned to broadcast the data. At step 1620, the microcontroller 1512 waits two seconds for an ACK message from the receiving transceiver (e.g. the transceiver of a portable nurse station 2310 or external device 428, shown in FIG. 4) indicating that the message has been received.

If, at step 1622, an ACK is received during the two second interval, the microcontroller 1512, at step 1624, sends an ACK message to the central computer 432, decrements the COMMAND COUNT to point to the next command and transfers control to step 1609 to retrieve the next command from the message. Otherwise, at step 1626, the microcontroller 1512 sends a NAK message to the central computer and branches to step 1609 to retry the current command. In this embodiment of the invention, the central computer 432 is programmed to allow a fixed number of retries (consecutive NAK messages) and then to retransmit the command message to the stationary transceiver.

At step 1616, if the selected command is not a transmit data command, step 1628 is executed to determine if it is a receive data command. If so, the microcontroller 1512 sends a read data message to the transmitter 1514 and conditions the transmitter to broadcast the message. Step 1630 then transfers control to step 1620, described above.

Steps 1620, 1622, 1624 and 1626 operate in the same manner for the receive data message as for the transmit data message except that step 1624 sends the data to the central computer 432 via the network server 430 and an ACK message to the other transceivers, while step 1626 sends NAK messages to both the other transceivers and the central computer 432. The microcontroller 1512 does not check for parity errors or checksum errors in the received data. These checks are performed at the central computer when it receives the data.

If, at step 1628, the command is not a receive data command, then it is an unknown command. In this instance, the microcontroller 1512 sends a NAK message to the central computer 432, decrements the command count and then branches to step 1609 to get the next command.

The process illustrated in FIG. 16a runs on the microcontroller 1512 in a continuous loop. This process is continually interrupted by a signal received from one of the badge transmitters which continually transmit their identification signals. Emergency alert messages or response messages generated by pressing the button 1118 on the badge transmitter 1111, shown in FIG. 11, occur only occasionally and should not be able to be confused with any other data messages. Thus, the microcontroller 1512 includes an unmaskable interrupt which is caused when the RF receiver receives a message. In this instance, at step 1650 of FIG. 16b, the interrupt is sensed and in response to this interrupt, at step 1656, the identification information from the badge and the location of the fixed transceiver which received the information are sent to the central computer 432.

Figure 17B:
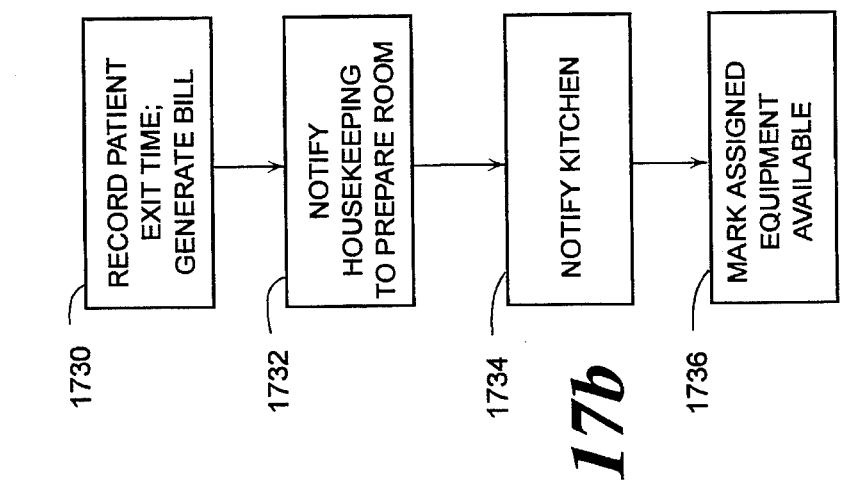
FIGS. 17a and 17b are flow-chart diagrams which illustrate the handling of patient entry and patient exit using a hospital monitoring system that includes an embodiment of the present invention.
Figure 17A:
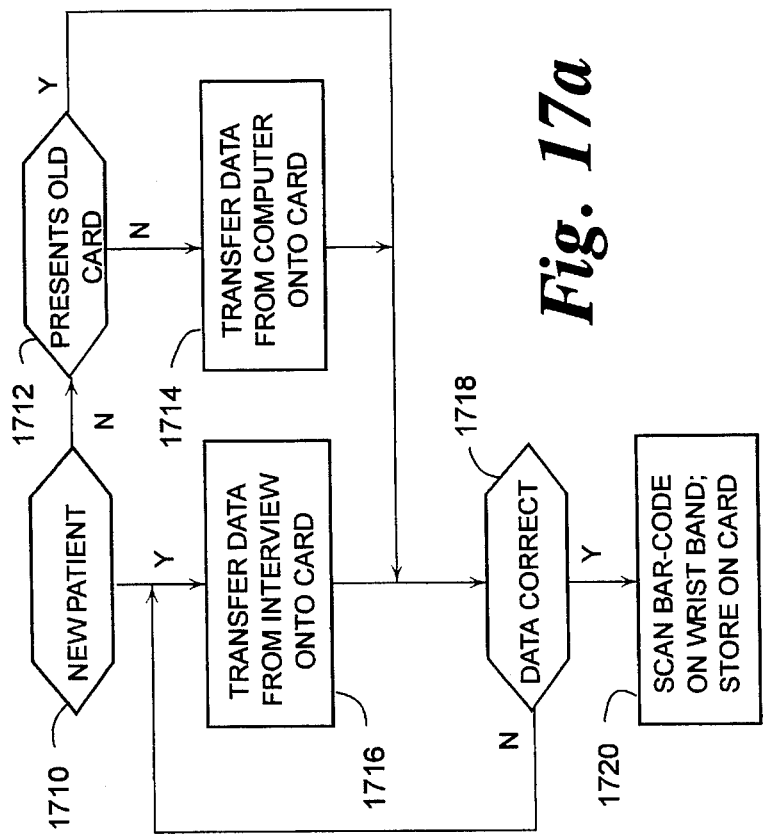

The discussion of FIGS. 1–16b above has described various components of a distributed processing network in which information on individuals and important equipment is stored on a personal database that is kept in close proximity to the individual or equipment. FIGS. 17a through 17d illustrate four exemplary functions that may be performed using this network. FIGS. 17a and 17b describe steps performed when the patient enters and leaves the hospital, FIG. 17c describes a process for locating equipment and personnel, and FIG. 17d describes a process for automating the assembly of teams of specialists to handle an emergency situation such as a "code blue."

At step 1710 of FIG. 17a, when a patient enters the hospital he may already have been issued a memory card 110. If so, at step 1712, he may have the card in his possession, in which case he presents it, or he may not have the card. If he does not have the card, step 1714 is executed which transfers an image of the card data as of the time the patient left the hospital, onto a new card. This stored data may be maintained in auxiliary data storage, such as a cartridge tape, coupled to the central computer 432. If, at step 1710, the patient has not been assigned a card, he is interviewed and, at 1716, the data from the interview is formatted and stored on a memory card. At step 1718, data on the card is printed so that the patient may examine and correct it. If any corrections are needed, step 1718 branches to step 1716 to enter the corrections.

After step 1718, when the patient has a card and the data on the card is correct, step 1720 is executed. In this step, an identifying wrist band, such as the band 140 described above in reference to FIG. 1d, is physically attached to the patient and the bar-code on the band is read and stored in the memory card.

When the patient is taken to his room, the card is inserted into the patient station 210 as set forth above in reference to FIG. 2 and the identification and other data is read from the card and stored locally in the card buffer area of the patient station, 210. If the card is removed, the data in this buffer is automatically invalidated and must be read from the card again. Accordingly, if the memory card 110 is a magnetic-stripe card, data in the buffer is desirably written onto the card before it is removed. This may be accomplished, for example, by requiring a button on the patient station to be pressed before the card may be removed. This button invokes a routine in the patient station microcomputer 414 which transfers the contents of the card buffer onto the card and then signals, for example, by causing a light to blink, that the card may be removed.

When the patient's food trays are prepared in the hospital kitchen, the central computer 432 is first checked to determine if the patient is still in his room (i.e. if his card is still engaged) and if his diet has been changed. This information is obtained directly from the patient station 210. When the tray is prepared, a sticker containing the patient's bar-code identification information and room number is attached to the tray. When the orderly delivers the tray, he scans the bar-code on the patient's wrist and the bar-code on the tray using the light pen at the patient station located near the patient's bed. If the bar-codes match, the patient station 210 emits an acknowledging beep and notifies the central computer that the tray has been delivered. If the bar-codes do not match, the patient station 210 emits an alarm tone. In this instance, the orderly may take the tray to the closest nurse station to determine what type of error occurred and how it may be corrected. Alternatively, this check could be performed by the orderly using a portable nurse station 2310 shown in FIGS. 4 and 23. The same procedure could be used to deliver radiographic images or medical test results to a patient's bedside.

Alternatively, if the patient card 110 has only limited memory storage capability, it may contain only the patient identification data and the data from the interview could be stored directly in central computer 432. In operation, when patient memory card is linked to a portable nurse unit or a patient station, this identification data is read from the card and transmitted via an infrared transmitter or other network link to a central nurse station and then to the server 430 and central computer 432. From this identification data, the already entered data could be downloaded temporarily to the sending unit and only maintained while memory card is coupled to the unit. Upon removal of the patient memory card from the particular unit being used, the downloaded patient information is desirably invalidated.

In FIG. 17b, when a patient leaves the hospital, he presents his card at the administration desk and the card is coupled to the central computer 432 which, at step 1730, records the exit time and generates billing information. At steps 1732 and 1734, the central computer notifies housekeeping and the hospital kitchen to prepare the bed for the next patient and to make no more food trays for the patient. Step 1736 checks for any equipment that was assigned to the patient and marks the equipment as being available in a central database.

Figure 17C:
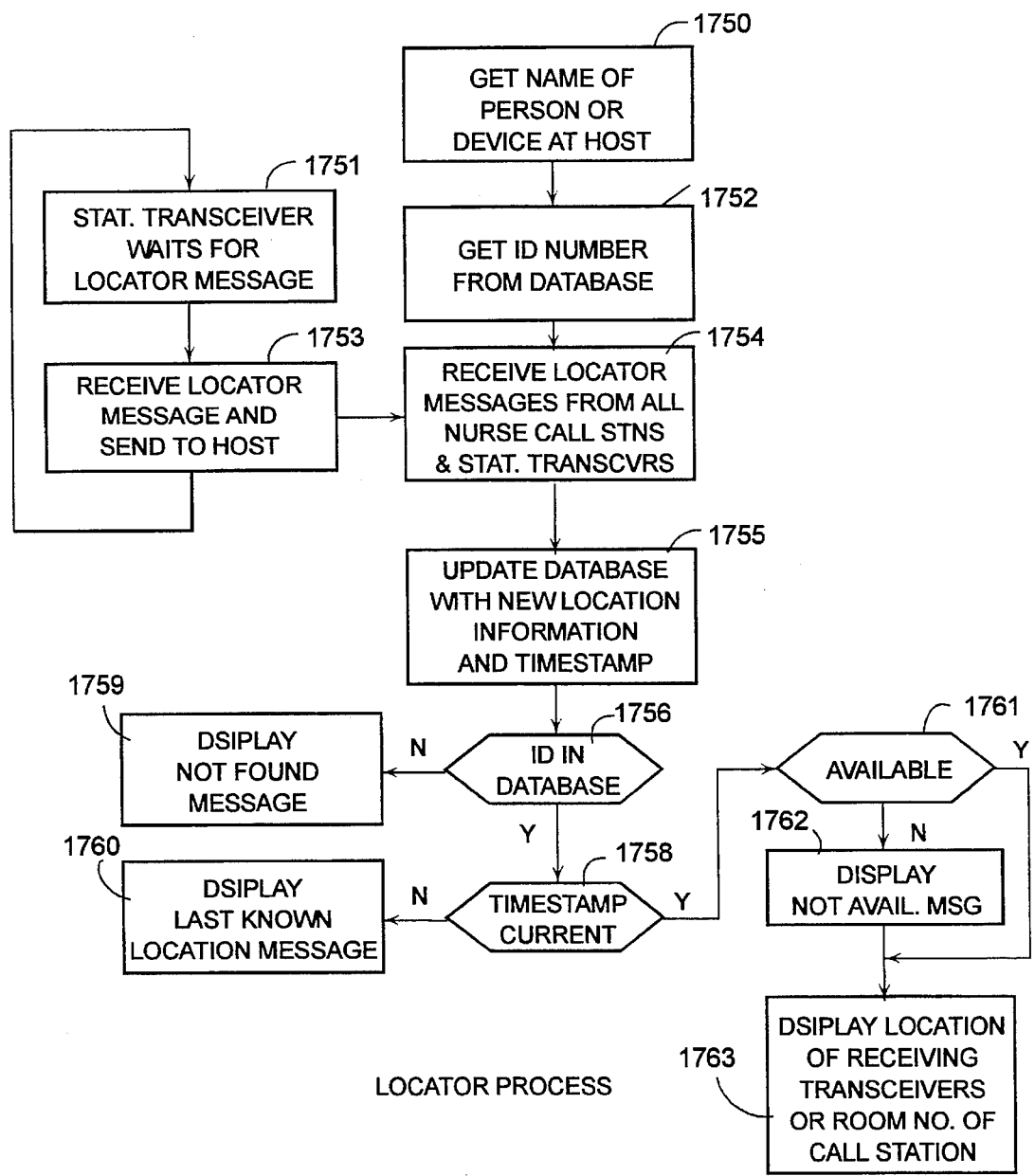

FIG. 17c illustrates how the memory cards 110 and 110' may be used in an automatic locator system. This is an automatic system because the identification badge continually transmits an identification signal and the central computer is continually monitoring these signals to update the location of the badge. Thus, this locator system does not require the computer to process a particular request before it locates an individual.

Referring to FIG. 17c, at step 1750 a user identifies the person or piece of equipment to be located to the central computer 432. At step 1752, the central computer searches the database for the entered name and finds the corresponding ID number.

As a continuing process, each of the stationary transceivers waits, at step 1751, to receive a locator message. When a person wearing a staff badge enters a room, the fixed transceiver in the room receives the transmitted ID number in a locator message and, at step 1753, sends the received ID number together with an address for the remote transceiver to the central computer 432. Patient identifiers and room numbers are sent to the central computer only when they are changed. That is to say when a patient card is either inserted into or removed from a patient station.

At step 1754, the central computer periodically receives messages from all of the fixed transceivers and from any of the patient stations which may have changed. At step 1755 it updates the entries in the data base to reflect the new location for each received ID number. Each location entry overwrites a previous entry and is marked with a timestamp. The two most recent locations are kept for each individual in the database. Using the two entries and their timestamps, the locator system can provide not only the location of the individual but his or her direction of travel as well.

At step 1756, the central computer determines if the ID number corresponding to the requested person or piece of equipment is in the database. If it is not, the central computer displays a message on the user's display terminal indicating that the requested entity is not present in the hospital.

If the ID number is in the database, the central computer, at step 1758 determines if the location entry is current. If not, that is to say if the timestamp is more than, for example, five minutes old, the central computer, at step 1760, displays a message indicating that the requested entity has not been located recently and indicates its last known location and direction of travel.

If the ID number of the requested entity is in the database with a current timestamp then the central computer, at step 1761, checks the database entry for the entity to determine if it is available. A piece of equipment may be marked as not available if it is currently being used. A person may be marked as unavailable if he or she is engaged in an important assignment, such as responding to a "code-blue" alert. If the requested entity is not available, the central computer displays a message to that effect as step 1762. If the entity is available, a message is displayed, at step 1763, indicating the current location of the entity.

The emergency alert process illustrated in FIG. 17d builds upon the locator process shown in FIG. 17c to produce a process that attempts to automatically assemble a team of specialists and equipment to respond to an emergency situation. In the first step in the process, step 1770, the central computer 432 determines the types of specialists and equipment that are needed. This information may be entered from a nurse station based on the condition of a patient. The condition may be sent to the nurse station with a patient initiated nurse call request, as set forth above, or it may be sent automatically when the patient station senses an alarm condition, such as an irregular heart beat, from data provided by external equipment.

It is contemplated that the nurse station would display a menu of, for example, five types of emergency situation, each requiring a different mix of personnel and equipment. One of these situations would be indicated to the central computer 432. This indication would provide the central computer with the types of specialists and equipment needed and an indication of which nurse station initiated the call.

Alternatively, an emergency alert may be generated by a caregiver pressing the switch 1118 on her badge transceiver. In this instance, a set of specialists and equipment would be assembled that could handle any situation.

At 1772, the computer 432 searches its personnel and equipment database to obtain a list of identifiers for each specialty type and for each type of equipment. At step 1774, the computer 432 uses the locator process shown in FIG. 17b to determine the location and availability of each individual and piece of equipment on each list. At step 1776, The computer conditions the PBX to ring the telephone set that is closest to the selected entities with a distinctive ring.

In response the distinctive ring someone near the telephone would answer it and either listen for the emergency message or see the message on the telephone's LCD display. If the requested individual has received the message, he may press the switch 1118 to indicate that he has responded. When this response is sensed, the computer 432 will add the person to the assembled team.

Otherwise, the requested person would be notified that he is needed by the individual who answers the phone. The requested person would acknowledge receiving the summons by pressing the button 1118 on his badge. If a piece of equipment is being requested, the individual who answers the phone may press the response button on the badge attached to the requested piece of equipment and send it to the requested location.

At step 1778, the central computer waits for a fixed amount of time, for example 30 seconds, to determine if all of the selected individuals and equipment have responded. If so, the responders are marked as unavailable and a full response message is displayed at the initiating nurse station 300 or at the nurse station closest to the individual who initiated the emergency alarm condition. This message includes a list of all of the equipment and personnel that have responded.

If, at step 1778, the central computer determines that some needed specialists or equipment have not responded, both the responding and non-responding entities are deleted from the lists. These lists are then passed to step 1774, described above, to locate the next closest specialists and equipment.

The processes outlined above illustrate a few applications of a distributed processing system which may be coupled to multiple personal databases. All of these applications are in a hospital environment. A system of this type has significant medical and non-medical uses outside of a hospital environment.

Figure 18:
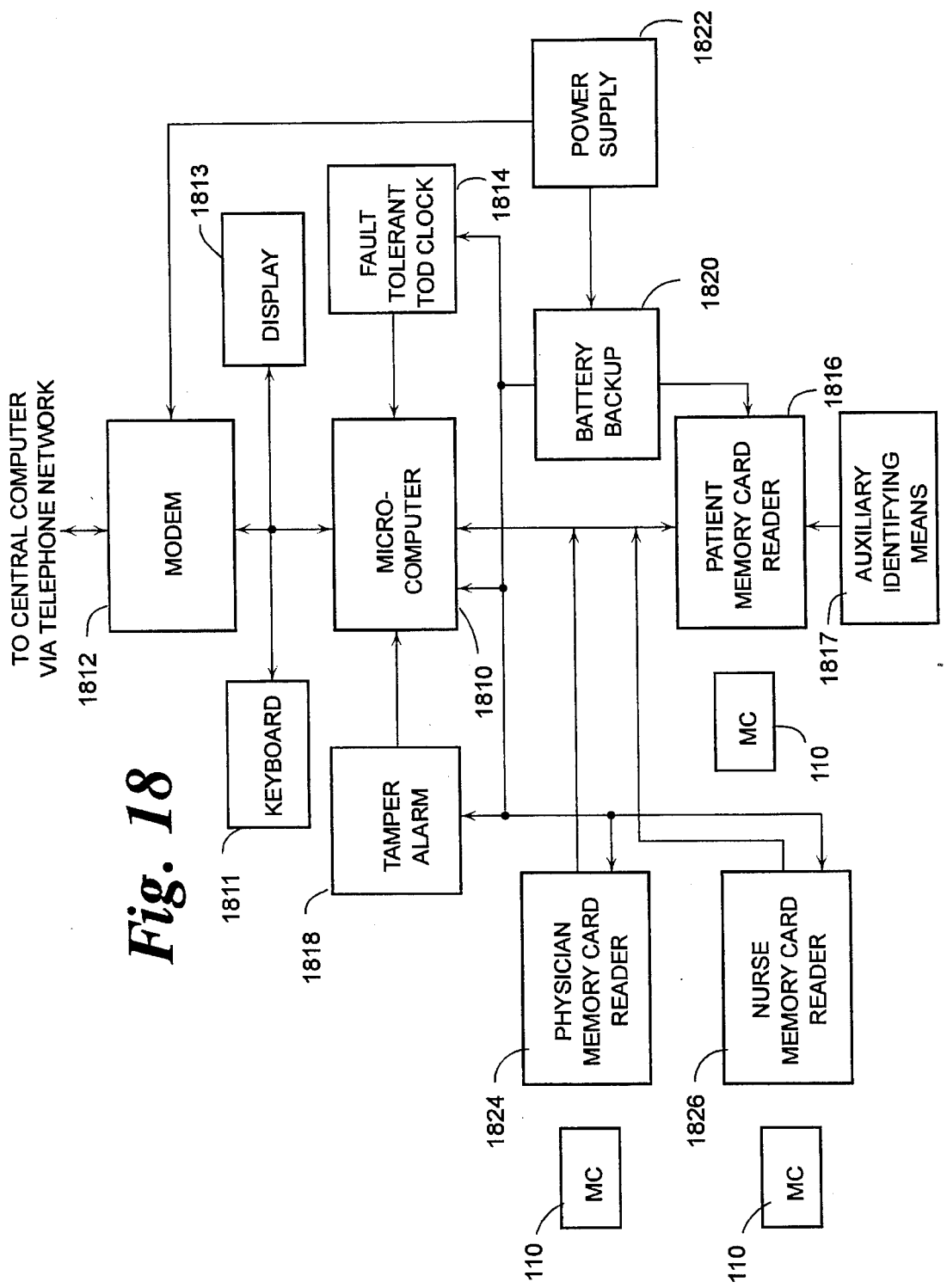
FIG. 18 is a block diagram of a system which monitors physician services and which includes an embodiment of the present invention.

FIG. 18 is a block diagram of a secure billing system for physicians and other professionals whose charges are based on the amount of time spent with a patient or client. To simplify the description, it is assumed that the system is located in a physician's office and is used for billing Medicare for services provided by the physician.

In general terms, the system operates as follows. Each physician would be provided with one system. When the physician is attending to each patient, that patient's card is inserted into the system. Also, the card of a third party, for example, an attending nurse, is inserted to the system. The system records identifying information from the cards and is provided, either by the doctor or by other office personnel with a diagnosis for the individual. The reason for the third party card is to reduce the possibility of fraud, and to provide an identifiable corroborating witness.

At the end of the day, the system automatically dials up a central computer and transfer the day's billing information. This information is then processed to determine the amount due to the physician. This type of system would speed the processing of Medicare bills by eliminating much of the paper work. In addition, it is advantageous because it is more difficult to generate fraudulent bills using a system of this type.

As shown in FIG. 18, an exemplary system of this type includes a microcomputer 1810 which is coupled to a modem 1812 through which data may be communicated to the central database. In addition, the microcomputer 1810 is coupled to a keyboard 1811 and display device 1813 which may be used to enter data, such as a diagnosis or prescription information into the computer system. These components exist in many commercially available personal computer systems, for example, those that are compatible with the IBM Personal Computer.

In addition to these basic computer components, the system shown in FIG. 18 includes a fault tolerant time of day (TOD) clock 1814, a tamper alarm system 1818, a patient memory card reader 1816, two staff memory card readers 1824 and 1826, and a power supply 1822 with a battery backup 1820. The system may also include auxiliary identifying means 1817, such as a commercially available fingerprint reader which can compare a person's fingerprint against data describing the fingerprint which is stored on the memory card 110.

The fault tolerant TOD clock 1814, tamper alarm system 1818 and battery backup 1820 ensure that the data provided by the billing system is accurate. The fault tolerant clock may be, for example, of the type described in a paper by D. Davies et al. entitled "Synchronization and Matching in Redundant Systems", IEEE Trans. on Computers, June, 1978, pp 531–539, which is hereby incorporated by reference. The nature of the tamper alarm system would depend on the construction of the overall billing unit. At a minimum, the tamper alarm would detect: any attempt to open the case enclosing the unit and the insertion of an object other than a data card into the data card reader. Any detected tampering would condition the system to both sound an audible alarm and record the tampering event. Optionally, the tamper alarm system could also disable the device. Any recorded tampering events are sent to the central database with the billing information.

The power supply 1822 and battery backup 1820 provide power to the tamper alarm 1818, microcomputer 1810, fault tolerant clock 1814, patient card reader 1816 and staff memory card readers 1824 and 1826 even when no power is applied to the billing unit. The power supply and battery backup may be any of a number of commercially available components. The exact type of components used would depend on the power requirements of the system and on the types of interruption that may be expected.

Figure 19:
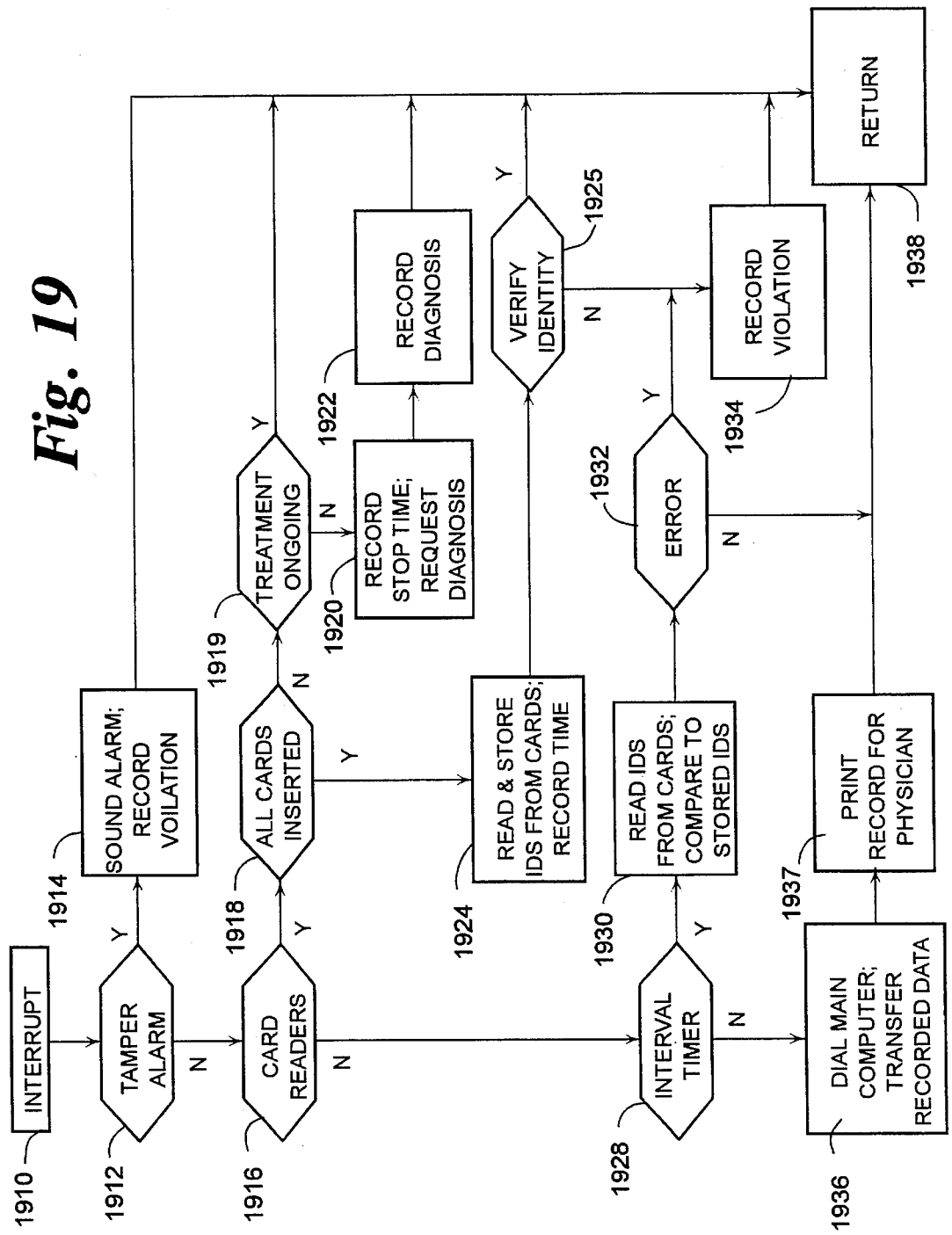
FIG. 19 is a flow-chart diagram which illustrates the operation of the monitoring system shown in FIG. 18.

FIG. 19 is a flow-chart diagram which illustrates the program that controls the billing system shown in FIG. 18. This program is desirably stored on ROM located securely within the case of the unit. The process shown in FIG. 19 operates in the background of other processing performed on the microcomputer 1810. Thus, the entire unit may be sold as a general purpose computer system for word processing or general billing. while the automatic billing function runs in a background mode.

In this configuration, care must be taken to ensure that no program which can interfere with the automatic billing operations is allowed to run on the system.

The first step in the program, step 1910, receives an interrupt. The interrupt may be from the tamper alarm 1818, patient memory card reader 1816, staff memory card reader 1830, or fault-tolerant TOD clock 1814. If, at step 1912, the interrupt is from the tamper alarm, step 1914 is executed which sounds the audible alarm and records the tampering event. After recording the tampering event, the process, at step 1938, returns control to the program that was running when the interrupt occurred.

If, at step 1916, the interrupt is caused by any of the memory card readers 1816, 1824 or 1826, step 1918 is executed to determine if all cards are inserted. If all cards are present, then a card has just been inserted, step 1924 is executed to read the identifying information from all of the cards and store this information and the current time for later transmission to the central database. Optionally, after step 1924 has been executed, step 1925 may be invoked to verify the identity of the patient and the attending physician. In the exemplary embodiment, this identification is accomplished by comparing fingerprint information stored on the cards with the actual fingerprint of the patient and the physician. If the identity is verified, control is transferred to step 1938, described above. Otherwise, a violation is recorded at step 1934 and control is returned to the foreground program at step 1938.

If, at step 1918, the patient card reader interrupt occurs when less than all of the cards are inserted, step 1919 is executed to determine if a treatment is currently in progress. If so, then one of the patient card, physician card or nurse card was removed to cause the interrupt. In this instance, step 1920 is executed to terminate the treatment, record the stop time and request a diagnosis for the patient. Either the physician or other office personnel enters the diagnosis which is recorded at step 1922. After step 1922, control is transferred to step 1938, described above. If, at step 1919, a treatment was not in progress and at least one card is missing, control is returned to the foreground program via step 1938 to await the insertion of the remaining card or cards.

In the exemplary embodiment of the invention, if the interrupt is not caused by the tamper alarm or one of the card readers, then it must be caused by the clock circuit 1814. At step 1928, the process determines if the clock interrupt is from the interval timer. If so, step 1930 is executed to read the identification information from each of the cards and compare it to the stored identification for each individual. If any difference is detected at step 1932, a violation is recorded at step 1934. After step 1934 or if no error is detected at step 1932, control is transferred to step 1938.

If the clock interrupt is not an interval timer interrupt then it is an indication that it is time to transfer the accumulated billing data to the main computer. In this instance, step 1936 is executed. This step dials the main computer and transfers the recorded data along with data identifying the physician. In addition, the computer, at step 1937, may condition a printer (not shown) to print out a record of the data transferred for the physician's records. After step 1937, control is transferred to step 1938 to return control to the program running at the time the interrupt occurred.

The system described above in reference to FIGS. 1–16 may be used in a hospital environment to monitor the usage of controlled substances such as prescription drugs. FIGS. 20a through 20e illustrate an exemplary system for auditing drugs which are stored in a drug locker. The invention does not significantly impede the access of individuals to the drug locker, unlike if using normal physical security measures such as a locker from heavy gauge steel and placing a lock on the door.

FIG. 20a is a cut-away top plan view of a drug locker 2010 in accordance with this embodiment of the invention. As shown, the drug locker is a physically secure cabinet, having a door 2011 that may be locked by lock 2012 and containing several medicine containers 130. A stationary transceiver 2014 of the type described above with reference to FIG. 15 is positioned close to the drug locker. This stationary transceiver, however, is coupled to receive signals from a keyboard unit 2015. In addition, inside the locker a bar-code reader 2016 is positioned next to the door 2011 and a removal detector 2018 is concealed in the floor of the locker, positioned so that any containers removed from the locker must be passed over the detector 2018.

The detector 2018 may be a resonance detector of the type commonly found in libraries and retail stores which detects an induced resonant signal in a passive reactive component 2022 attached to the bottom of each medicine container 130, as shown in FIG. 20c.

FIG. 20b is a functional block diagram of the drug monitoring system used in the drug locker. In addition to the components shown in FIG. 20a, the system shown in FIG. 20b includes an audible alarm 2021, indicator lights and a door open detector 2019. All of the system elements 2016 through 2021 are configured to be controlled by the microcontroller 1512 of the stationary transceiver, as shown in FIG. 15. The stationary transceiver is, in turn, in communication with and controlled by server 430 and central computer 432.

FIG. 20d is a flow-chart diagram which illustrates the portion of the drug audit process that utilizes the circuitry shown in FIG. 20b. At step 2050, whenever a badge transmitter normally worn by a hospital staff member is within a preset distance, for example, one meter of fixed transceiver 2014, the transceiver receives the identification signal from the badge at step 2052. Next, at step 2057, the keyboard and display unit 2015 prompts for a personal identification number (PIN) stored in the central computer 432 as being associated with this badge. This PIN may be the same number as is used to obtain the badge from the base unit or, for enhanced security it may be a different number.

At step 2058, the transceiver sends a request to the central computer 432 to compare the identification signal and PIN with a predetermined list of authorized personnel. Alternatively, this compare operation may be performed using the microcontroller 1512 of the stationary transceiver 2014 using an authorized list that is either stored locally, at the server 430 or at central computer 432.

If, at step 2054, the ID signal is not found on the list, access to the drug locker is denied at step 2060 and the unauthorized attempted access will be recorded on central computer 432.

If at step 2058, the identification signal is found on the list and the PIN is proper, access is granted by fixed transceiver 2014 sending a signal to release lock 2012 on door 2011.

If the individual is authorized to access the locker, step 2064 records the identifying information and the authorization information on the central computer 432. As each medicine container is removed from the locker, it is scanned by the bar-code reader. When the bar-code information has been scanned, the process changes a value in a memory location to indicate that the container may be removed.

The actual use of the prescription medicines may also be monitored from the information provided to the central computer 432. This information indicates the individuals who had access to the drug locker, the time they removed and returned the medicines, the patients to whom the medicines were administered, the prescribed doses and, optionally, the amount of medicine that was removed and the amount that was returned. This entire auditing process could take place without significantly impeding access to the drug locker.

FIG. 20e illustrates the process of monitoring the distribution of medicine that is obtained in step 20d. The steps in this process are executed as the medicine is given to the patients. At step 2080, the nurse scans the patient bar-code on the wrist band 140 using either the patient station bar-code reader or the portable nurse station bar-code reader. Next, at step 2082, the bar-code on the medication is scanned. At step 2086, either the patient station computer 414 or the central computer 432, both shown in FIG. 4, compares the medication information with stored prescription information for the patient. If a match is found, then, at step 2090, the prescribed dosage of the medicine is recorded in the central computer 432 as having been distributed and the administration of the medication is recorded in the patient's record in the central computer, patient station computer and, optionally, on the patient's memory card.

All of the applications described above relate in some manner to the health care field. It is contemplated, however, that significant applications for the invention exist in areas other than health care. FIGS. 21a and 21b relate to an application of the invention which establishes a student information link in through a special telephone set in the student's dormitory room.

Figure 21B:
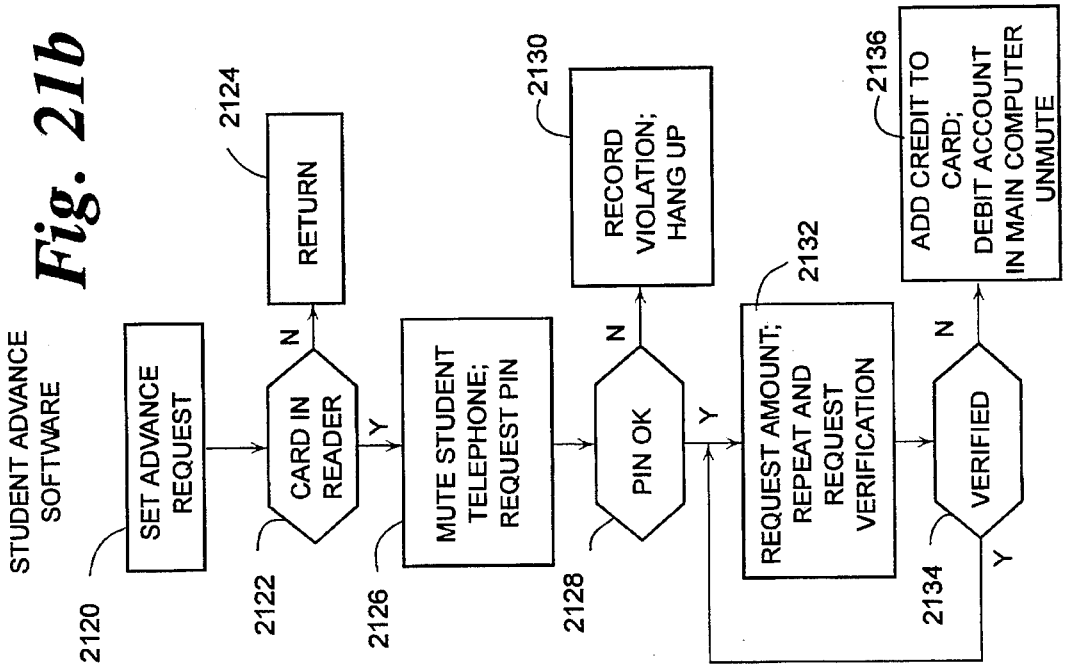
Figure 21A:
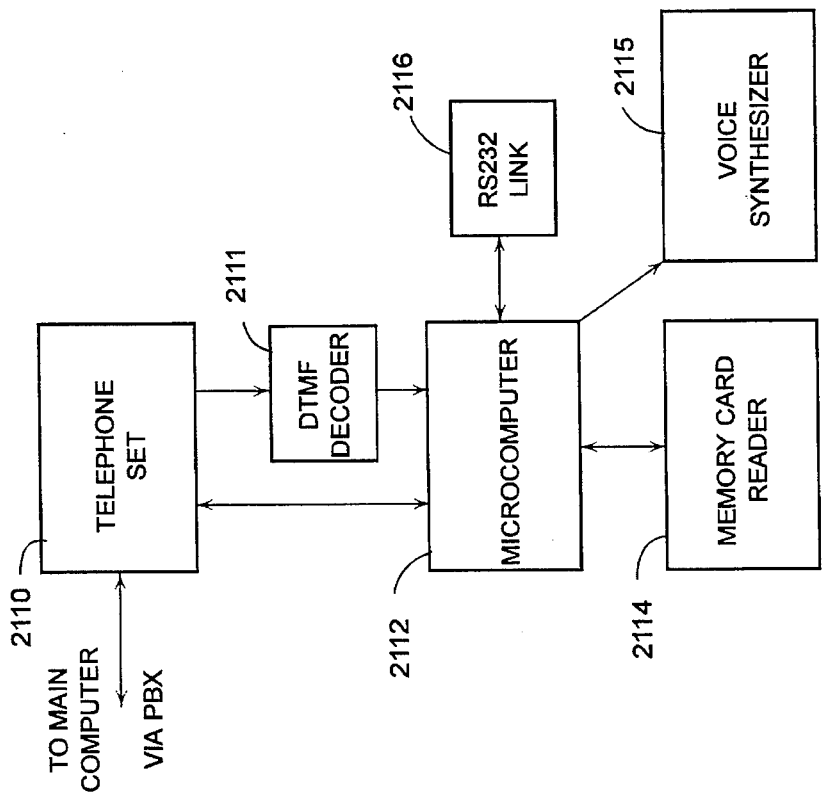
FIG. 21a is a block diagram of a student information system which includes an embodiment of the present invention.

As shown in FIG. 21a, the telephone set 2110 is coupled to a dual-tone multifrequency (DTMF) decoder 2111, microcomputer 2112, a memory card reader/writer 2114, a voice synthesizer and a digital data port, such as an RS232 link 2116. A data link between a central computer (not shown) or network server (not shown), the memory card reader/writer 2114 and the RS232 link 2116 is established through the telephone set 2110 which is coupled to a PBX (not shown).

In this configuration, the memory card may be used as a standard identification card for directly billing telephone calls or to allow access to student records, assignment information, or a student bulletin board, via a personal computer coupled to the RS232 port.

In addition, the memory card may be used for a novel form of electronic funds transfer (EFT) as illustrated in FIG. 21b. The following scenario illustrates how this system may be used. The student and the parent are in a discussion and the student requests funds from his parents. At step 2120, the parent enters an initial code by depressing a particular sequence of buttons on the telephone. At step 2122, the microcomputer 2122 determines if the card is in the reader. If it is not, a distinctive tone or a voice message from the synthesizer 2115 is emitted and the telephone conversation continues normally.

If, however, at step 2122, the card is in the reader 2114, step 2126 is executed in which the student telephone is muted and the voice synthesizer 2115 is used to prompt the parent for a personal identification number (PIN). At step 2128, if the PIN is correct, the voice synthesizer requests the parent to enter an amount to enter on the debit card, repeats the request using the voice synthesizer and requests verification from the parent. If, at step 2134, the parent verifies the amount entered at step 2132, step 2136 is executed in which the amount is added as a credit to the debit card and a debit entry is made on a bill to be sent to the parents. If the amount is not verified at step 2134, control is transferred to step 2132 for the parent to reenter the amount or to cancel the transaction.

If the PIN is not correct at step 2128, step 2130 is executed in which the microcomputer 2112 records a violation on the central computer 432 and either unmutes the student telephone allowing the conversation to resume, or disconnects the telephone.

In this embodiment of the invention, the credit on the card may be used only at specified locations on campus, for example, at the book store. As the funds are spent, a record is made of the purchases and this record is sent to the parent along with the debit entry on the next account statement.

It is also contemplated that a locator and emergency alert system such as described above in reference to FIGS. 11 through 17 may be used in a corrections environment to determine the location of prison guards and trustees and to allow a prison guard to signal an emergency alert. This locator system may also be used as an automatic key station. For this use of the system, a network of the same type as the network N2 shown in FIG. 14 may be set up inside of a factory or office building. In this network, each of the stationary transmitters is programmed to continually receive identification messages transmitted by the badges. As a guard, wearing a badge transmitter passes the transceivers, the identity information is transmitted from the card and stored in a central computer as passing through the transceiver. This system has advantages over the traditional key station system since the guard need not carry the bulky clock device and since the location of the stationary transceivers may be concealed making it more difficult for the guard to defeat the system by taking a different route.

While the invention has been described in terms of several exemplary embodiments, it is contemplated that it may be practiced with modifications within the spirit and scope of the appended claims.

What is claimed is:

1. Apparatus for automating routine communication and location determination, comprising:

a plurality of badges, each having: a database memory, removably coupled to said badge, for storing information including information specific to one of a plurality of users; a transmitter for wirelessly transmitting a portion of said information including said specific information; a badge switch for activating said badge; and a processor for controlling said transmitter and coordinating retrieval and transmission of said portion of said information;

a plurality of transceivers each being connected to a network server and each being disposed at preassigned locations to cover a predetermined range for receiving wireless transmissions from said badges within said range and for transmitting to said network server messages about said received wireless transmissions; and a central processor being connected to said network server having:

means for receiving information about badges which have been activated and their respective users and said messages from said transceivers through said network server; means for processing said messages for updating said information about said badges and their associated users; and a display for displaying said updated information.

2. The apparatus according to claim 1 wherein each of said badges includes means for mating a card for switching said badge switch for activating said badge when said card is mated to said badge.

3. The apparatus according to claim 1 wherein said badge switch is connected to said processor whereby when said badge switch is depressed said processor causes said transmitter to transmit signals indicating a preassigned condition.

4. The apparatus according to claim 1 wherein said display of said updated information includes the location of said badges and their associated users.

5. The apparatus according to claim 1 wherein said display of said updated information includes the availability of said users.

6. The apparatus according to claim 1 wherein said network server includes a private branch exchange (PBX) for connection to a plurality of telephones.

7. The apparatus according to claim 1 further including a base unit having storage of information including information specific to each of a plurality of users and means for reading and writing data in and out of said databases of said badges.

8. The apparatus according to claim 7 wherein said data includes the identity of the user to be associated with a badge.

9. The apparatus according to claim 8 wherein said base unit includes means for informing said central processor that a badge has been written with the identity of an associated user.

10. The apparatus according to claim 1 wherein each of said badges includes a receiver for receiving data.

11. The apparatus according to claim 1 wherein said central processor includes memory for storing information about badges which have been activated and their respective objects.

12. Apparatus for automating routine communication and location determination, comprising:

a plurality of badges, each having: a database memory for storing information about a user associated with the badge; a transmitter for wirelessly transmitting a portion of said information; a badge switch for activating said badge; and a processor for controlling said transmitter and coordinating retrieval and transmission of said portion of said information;

a plurality of transceivers each being connected to a network server and each being disposed at preassigned locations to cover a predetermined range for receiving wireless transmissions from said badges within said range and for transmitting to said network server messages about said received wireless transmissions; and a central processor being connected to said network server having:

means for receiving information about badges which have been activated and their respective users and said messages from said transceivers through said network server; means for processing said messages for updating said information about said badges and their associated users; and a display for displaying said updated information;

said badge switch is connected to said processor whereby when said badge switch is depressed said processor causes said transmitter to transmit signals indicating a preassigned condition;

wherein said processor includes means for causing said transmitter to transmit signals indicating different preassigned conditions depending upon the sequence of said switch depressions.

13. Apparatus for automating routine communication and location determination, comprising:

a plurality of badges, each being removably coupled to an individual and each having: a database memory, removably coupled to said badge, for storing information including identity information about the respective individual; a transmitter for wirelessly transmitting a portion of said information stored in said memory including said identity information; and a processor having associated stored programs for coordinating the transfer and transmission of said portion of said information;

a plurality of transceivers, each being spatially disposed to cover a respective area, each having: a receiver for receiving said portion of said information transmitted from a badge within said respective area; an interface for interfacing said transceiver to a central processing unit; a transmitter for transmitting messages including said information received from said badges to said central processing unit through said interface; and a processor for coordinating said reception of said portion of said information and for coordinating said interface between said receiver and said central processing unit;

said central processing unit includes a processor for receiving and processing data received from said plurality of transceivers for determining the location of each of said individuals; and wherein each of said plurality of badges includes means for transmitting said identity information at a substantially periodic time interval.

14. Apparatus according to claim 13 wherein said database memory is nonvolatile.

15. Apparatus according to claim 14 wherein said nonvolatile memory is an electronically erasable read only memory.

16. Apparatus according to claim 13 further including a base unit having means for reading and writing information including said identity information in and out of the database memory of said badges.

17. Apparatus according to claims 16 wherein said base unit includes means for calculating, storing and displaying an amount of time during which said database memory is coupled to said respective badge.

18. Apparatus according to claim 13 wherein said central processing unit includes means for determining a most recent direction of travel of each of said individuals.

19. Apparatus according to claim 13 wherein said central processing unit includes central memory for storage of information including the identity of each of said plurality of badges and each individual being coupled thereto.

20. Apparatus according to claim 13 wherein said central processing unit further includes means for periodically updating the locations of each of said badges and their respective individuals.

21. Apparatus according to claim 13, wherein said means for updating further includes updating time stamp and availability information.

22. Apparatus according to claim 13, further including identification verification means coupled to each of said plurality of transceivers and responsive to said identification signal, for automatically prompting said identified individual to enter a personal identification code, for comparing said entered personal identification code with previously stored identification codes and for transmitting a signal to allow access to a secured area if said identification code is equivalent to one of said previously stored identification codes.

23. Apparatus according to claim 13 wherein each of said plurality of badges is adapted to mate with a card, each of said badges further includes a switch for turning off said badges if said card is detached from said respective badge.

24. Apparatus according to claim 13 wherein said badge includes a receiver for receiving data.

25. Apparatus according to claim 13 wherein said database memory includes medical information pertaining to the individual associated with the badge.

26. Apparatus according to claim 13 further including an input device by which a user may enter data and means for transmitting the entered data to said central processing unit by way of said transceivers.

27. Apparatus according to claim 13 wherein said badge further includes a switch whereby when said switch is depressed, said badge transmits a predetermined signal representing a preassigned condition.

28. Apparatus according to claim 27 wherein said predetermined signal is activated to acknowledge receipt of signals from said transceiver.

29. Apparatus according to claim 13 wherein said interface is coupled to a telephone switching system for connection to a plurality of telephones for communicating with individuals located by said apparatus.

30. Apparatus for automating routine communication and location determination, comprising:

a plurality of portable communicator means, each having: database memory means, removably coupled to said portable communicator means, for storing information including information specific to one of a plurality of users; transmitter means for wirelessly transmitting a portion of said information including said specific information; switch means for activating said badge; and processor means for controlling said transmitter means and coordinating retrieval and transmission of said portion of said information;

a plurality of transceiver means, each being disposed at preassigned locations to cover a predetermined range for receiving wireless transmissions from said portable communicator means within said range and for forwarding to a central processor messages about said received wireless transmissions; and said central processor having means for receiving information about portable communicator means which have been activated and their respective users and said messages from said plurality of transceiver means; means for processing said messages for updating said information about said portable communicator means and their associated users; and a display for displaying said updated information.

* * * * *